(12) United States Patent
Grenda et al.

(10) Patent No.: US 8,907,130 B2
(45) Date of Patent: Dec. 9, 2014

(54) BETA-HYDROXYALKYLAMIDES, METHOD FOR THEIR PRODUCTION AND USE THEREOF

(75) Inventors: Werner Grenda, Herne (DE); Emmanouil Spyrou, Schermbeck (DE); Thomas Weihrauch, Duelmen (DE); Christoph Lammers, Recklinghausen (DE); Holger Loesch, Herne (DE); Klaus Behrendt, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/583,826

(22) PCT Filed: Mar. 10, 2011

(86) PCT No.: PCT/EP2011/053606
§ 371 (c)(1),
(2), (4) Date: Sep. 10, 2012

(87) PCT Pub. No.: WO2011/110624
PCT Pub. Date: Sep. 15, 2011

(65) Prior Publication Data
US 2013/0006016 A1  Jan. 3, 2013

(30) Foreign Application Priority Data

Mar. 11, 2010  (DE) .................. 10 2010 002 783

(51) Int. Cl.
*C07C 231/00* (2006.01)
*C07C 233/60* (2006.01)
*C07C 231/02* (2006.01)

(52) U.S. Cl.
CPC .............. *C07C 231/02* (2013.01); *C07C 233/60* (2013.01); *Y10S 525/934* (2013.01)
USPC .............. 564/134; 428/481; 524/81; 524/401; 525/420; 525/425; 525/437; 525/934; 528/296; 528/298; 528/301; 528/302; 528/307; 528/308; 528/308.6; 564/138

(58) Field of Classification Search
USPC ............ 428/481; 524/81, 401; 525/420, 425, 525/437, 934; 528/296, 298, 300, 301, 302, 528/307, 308, 308.6; 564/134, 138
See application file for complete search history.

(56) References Cited

U.S. PATENT DOCUMENTS

| | | | |
|---|---|---|---|
| 8,476,376 B2 * | 7/2013 | Grenda et al. ................ | 525/374 |
| 8,524,837 B2 * | 9/2013 | Grenda et al. ................ | 525/374 |
| 2008/0255272 A1 | 10/2008 | Weiss et al. | |
| 2011/0039981 A1 | 2/2011 | Hefner et al. | |
| 2011/0224378 A1 | 9/2011 | Grenda et al. | |
| 2011/0224459 A1 | 9/2011 | Grenda et al. | |
| 2011/0288202 A1 | 11/2011 | Grenda et al. | |

FOREIGN PATENT DOCUMENTS

| | | | |
|---|---|---|---|
| JP | 49 26226 | 3/1974 | |
| KR | 10-2009-0111720 | * 10/2009 | ............ C07C 233/58 |
| KR | 10 2009 0111720 | 10/2009 | |
| WO | 2009 143037 | 11/2009 | |

OTHER PUBLICATIONS

Jung, H.R., et al.; J. Korean Ind. Eng. Chem., vol. 20, No. 2, Apr. 2009, p. 195-200.*
English Translation of Jung, H.R., et al; J. Korean Ind. Eng. Chem., vol. 20, No. 2, Apr. 2009, p. 195-200; Translation numbered p. 1-20.*
U.S. Appl. No. 13/583,252, filed Sep. 10, 2012, Grenda, et al.
Jung, H. R., et al., "Preparation and Properties of $N^1$, $N^1$, N4, N4-Tetrakis (hydroxyethyl)cyclohexane-trans-1,4-dicarboxamide as a Crosslinker of Polyester Powder Coatings," J. Korean Ind. Eng. Chem., vol. 20, No. 2, pp. 195 to 200, (Apr. 2009) XP 9148131(with English abstract).
International Search Report Issued Jun. 9, 2011 in PCT/EP11/053606 Filed Mar. 10, 2011.
Jung, H-R., et al, "Preparation and Properties of $N^1 \cdot N^1 \cdot N^4 \cdot N^4$-Tetrakis(hydroxyethyl)cyclohexane-*trans*-1,4-dicarboxamide as a Crosslinker of Polyester Powder Coatings," *J. Korean Ind. Eng. Chem.*, vol. 20(2), Apr. 2009, p. 195-202. (English Translation).

* cited by examiner

*Primary Examiner* — Robert Jones, Jr.
(74) *Attorney, Agent, or Firm* — Oblon, Spivak, McClelland, Maier & Neustadt, L.L.P.

(57) ABSTRACT

The invention relates to novel β-hydroxyalkylamides, to a method for their production and to the use thereof.

42 Claims, 13 Drawing Sheets

Figure 5: DSC diagram of the ß-hydroxyalkylamide of the formula XIIA described in example 3a Figure 6: DSC diagram of the ß-hydroxyalkylamide of the formula XIIA described in example 3b Figure 7: DSC diagram of the ß-hydroxyalkylamide of the formula XIIA described in example 4b Figure 8: DSC diagram of the ß-hydroxyalkylamide described in example 4c Figure 9: XRPD (x-ray powder diffraction) analysis of the ß-hydroxyalkylamide of the formula XIIA described in example 3a (matting material)

Figure 10: XRPD (x-ray powder diffraction) analysis of the ß-hydroxyalkylamide described in example 4c (nonmatting material)

Figure 11: XRPD (x-ray powder diffraction) analysis of the ß-hydroxyalkylamide of the formula XIIA described in example 4b (matting material)

Figure 12: Ortep plot (50%) with numbering scheme

Calculated powder diffractogram based on the single-crystal structural determination of N,N,N',N'-tetrakis(2-hydroxyethyl)cyclohexyl-1,4-diamide (vesta sample)

BETA-HYDROXYALKYLAMIDES, METHOD FOR THEIR PRODUCTION AND USE THEREOF

The invention relates to new β-hydroxyalkylamides, to a method for preparing them, and to the use.

β-Hydroxyalkylamides are valuable intermediates in organic synthesis.

For ten years, p-hydroxyalkylamides have found technical applications in powder coating materials, as curing agents (also referred to as crosslinkers).

β-Hydroxyalkylamides and methods for preparing them are also known from the following patent documents: DE 25 09 237, DE 198 23 925, EP 0 473 380, EP 0 960 878, WO 2000050384, WO 200055266.

Powder coating materials based on triglycidyl isocyanurate (TGIC) as crosslinker (curing agent) and on acid-functional polyesters produce corrosion-resistant and weather-stable powder coatings. TGIC, however, is classed as mutagenic and toxic.

Toxicologically unobjectionable and at the same time also more reactive are β-hydroxyalkylamide crosslinkers. U.S. Pat. No. 4,076,917 and U.S. Pat. No. 4,101,606 combine β-hydroxyalkylamides with polymers having at least one carboxylate or anhydride function, more particularly with polyacrylates, to give powder coating materials. EP 0 322 834 describes thermosetting powder coating materials composed of 1'-hydroxyalkylamides and polyesters containing acid groups.

Considerable interest attaches to coating systems which give a substrate a uniformly even and matt surface. The reason for this is primarily practical. Glossy surfaces require a far higher degree of cleaning than matt surfaces. Furthermore, it may be desirable on safety grounds to avoid strongly reflecting surfaces. Across broad areas of application in the powder coatings industry, such as the architectural, automotive, and metal furniture segments, etc., there is increasing demand for matt (10-30 units) and semimatt (30-50 units) surfaces, measured as reflectometer values according to DIN 67530/ISO 2813 at an incident angle of 60°.

The simplest principle for obtaining a matt surface is to admix the powder coating material with smaller or larger amounts—depending on the extent of the desired matt effect—of fillers, such as chalk, finely divided silicon dioxide or barium sulfate, for example. These additions, however, produce a deterioration in the technical film properties, such as adhesion, flexibility, impact strength, and chemicals resistance.

The addition of substances incompatible with the coating material, such as waxes or cellulose derivatives, for example, does indeed result in matting, distinctly, but slight changes during the course of extrusion lead to fluctuations in the surface gloss and to fade-out in dark shades. The reproducibility of the matt effect is not ensured.

EP 0698645 describes producing matt powder coating materials by dry-blending at least two separately fabricated hydroxyalkylamide powder coating materials.

For semimatt and matt (<50 gloss units) powder coatings with hydroxyalkylamides, then, the state of the art comprises dry blends—in other words, it is necessary to produce, separately, two hydroxyalkylamide powder coating materials, with different acid numbers of the binder components, which are then supplied for grinding as a dry blend. This involves considerable extra cost and effort and, in the event of deviation in a binder component, leads to gloss deviations, which take considerable additional cost and effort to correct. Furthermore, these dry blends suffer separation, including at the premises of the end customer, with a resulting shift in gloss if the powder coating material is—as is usual—to be recycled.

The laid-open specification KR 10-2009-0111720 (application number 10-2008-0037454), translated title "CYCLOALKANE DICARBOXAMIDE COMPOUNDS, THEIR PREPARATION AND APPLICATION" (see also J. Korean Ind. Eng. Chem., Vol. 20, No. 2, April 2009, 195-200), discloses, in particular in example 1, the there-named compound $N^1,N^1,N^4,N^4$-tetrakis(2-hydroxyethyl)cyclohexane-1,4-dicarboxamide (formula 3). This compound according to FIG. 2 has only one peak by DSC analysis, with a maximum peak at approximately 190° C. A cis/trans content for the compound is not stated. Furthermore, polyesters containing carboxyl groups, which are not precisely defined but are indicated only by broad ranges for certain parameters (polyesters not unambiguously characterized and unknown on the market with this viscosity), are crosslinked with this compound and compared with the known β-hydroxyalkylamide, here identified in example 3 as $[N^1,N^1,N^6,N^6$-tetrakis(2-hydroxyethyl)adipamide] (available as VESTAGON HAA 320 or PRIMID XL 552), in other words with curing agents from the prior art and with long-established market products known to lead to glossy surfaces on the coatings produced. FIGS. 3 and 4 show the metal panels. No description is given to the effect that the coatings in question are matt coatings. Nor is this possible, since glossy coatings are obtained with the conventional curing agent.

It was an object of the present invention to find new β-hydroxyalkylamides which can be used as intermediates and curing agents. A particular object of the invention was to find new β-hydroxyalkylamides which in powder coating materials, after curing, lead to matt surfaces, and which do not require dry blending in the production of the powder coating materials.

This object has been achieved by the new β-hydroxyalkylamides of the invention.

BRIEF DESCRIPTION OF THE DRAWINGS

FIG. 5 is a DSC diagram of the β-hydroxyalkylamide of the formula XIIA described in example 3a.

Figure 1:
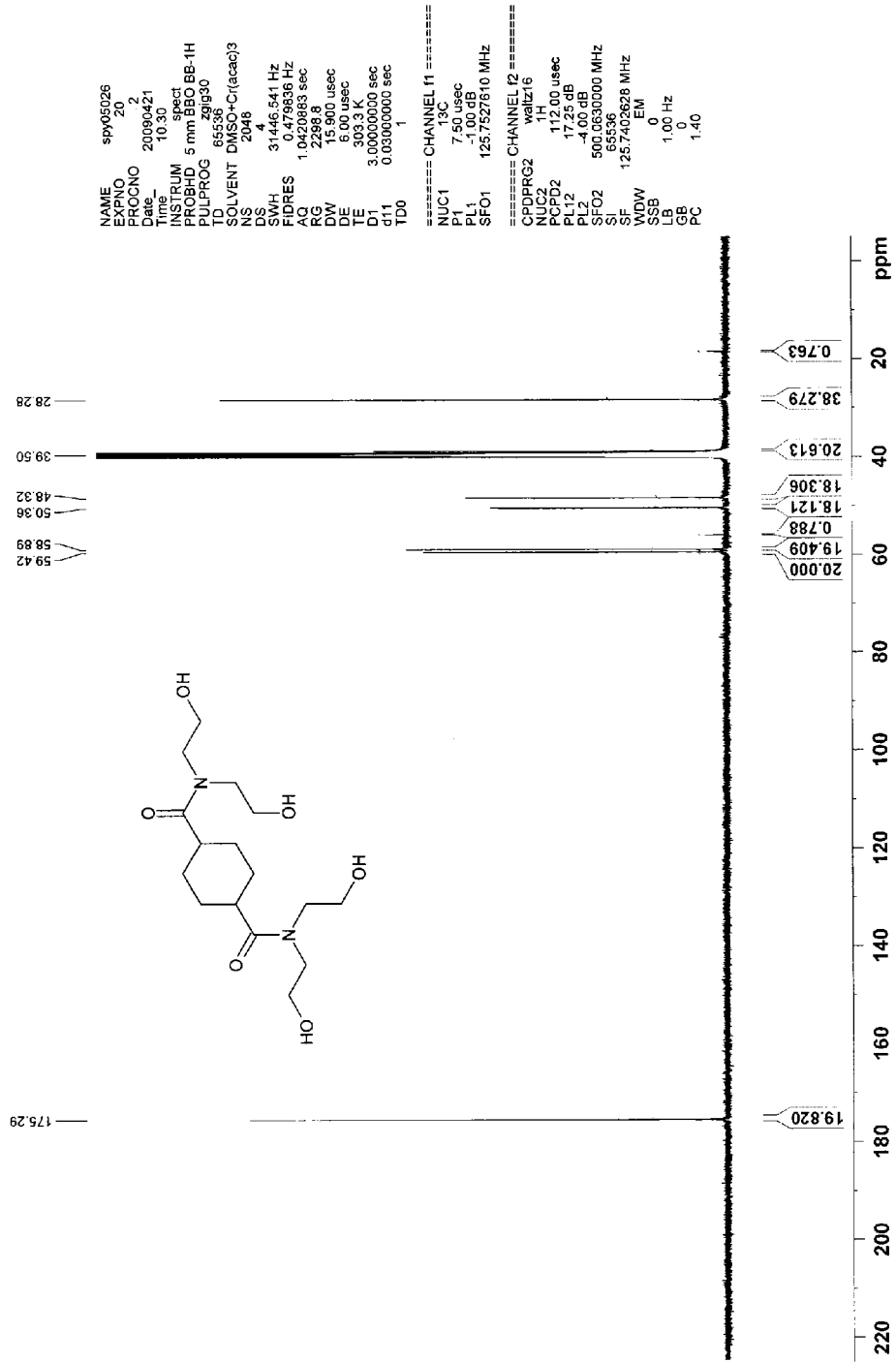
FIG. 1 is a $^{13}$C-NMR spectrum of the trans-N,N,N',N'-tetrakis(2-hydroxyethyl)cyclohexyl-1,4-diamide of formula XII.

The invention provides β-hydroxyalkylamides having two or three or four β-hydroxyalkyl amide groups per molecule of the formula I

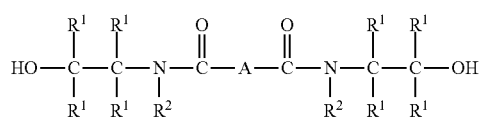

where
$R^1$ and $R^2$ independently of one another are identical or different radicals selected from alkyl radical, cycloalkyl radical, aryl radical, aralkyl radical or alkenyl radical having 1-24 carbon atoms, it also being possible for the radicals to contain heteroatoms and/or functional groups, and it also being possible for $R^1$ to be hydrogen,
and it also being possible for $R^2$ to be

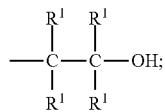

and
A is $A^1$

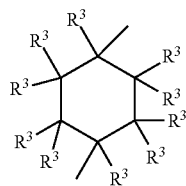

$A^2$

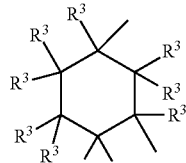

$A^3$

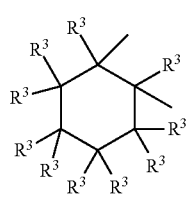

where radicals $R^3$ independently of one another are identical or different radicals selected from hydrogen, alkyl radical, cycloalkyl radical, aryl radical, aralkyl radical or alkenyl radical having 1-24 carbon atoms, it also being possible for the radicals to contain heteroatoms and/or functional groups, and it being possible for two or more substituents $R^3$ to be linked with one another to form rings; where the β-hydroxyalkylamides are present in solid form below 150° C.

Surprisingly it has been found that β-hydroxyalkylamides having a cyclohexane ring in the framework, and where the β-hydroxyalkylamides are present in solid form below 150° C., lead in powder coating materials, after curing, to matt surfaces. Furthermore, the β-hydroxyalkylamides of the invention represent new intermediates.

The β-hydroxyalkylamides can be prepared from various starting materials. A known reaction is that of β-hydroxyalkylamines with esters of carboxylic acids, the latter generating the parent structure (A). Depending on the selection of the starting materials, it is possible in this way to generate the β-hydroxyalkylamides of the invention.

Alternative but less preferred methods are based on other carboxylic acid derivatives, such as carboxylic acids, carbonyl chlorides, carboxylic anhydrides or other activated carboxylic acid derivatives as starting materials, which are reacted with β-hydroxyalkylamines.

Suitable β-hydroxyalkylamines are those which have alkyl groups having at least 2 to 10 carbon atoms in the hydrocarbon framework. The alkyl groups may be linear, branched or else cyclic. It is likewise possible for the alkyl groups to be substituted by heteroatoms, preferably oxygen, nitrogen. Furthermore, these alkyl groups may also contain functional groups, preferably carbonyl groups, carboxyl groups, amino groups, amide groups, urethane groups, and may carry an additional alkyl radical on the nitrogen.

In this invention the β-hydroxyalkylamides are preferably prepared from N-alkyl-1,2-alkanolamines and/or from N,N-bis-2-hydroxyalkylamines and esters of cyclohexanedicarboxylic acids.

Particular preference is given to using β-hydroxyalkylamines of the formula II and/or formulae II

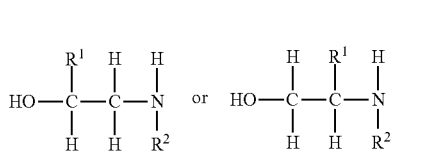

where
$R^1$ is hydrogen, methyl, ethyl, propyl,
$R^2$ is methyl;

formulae III

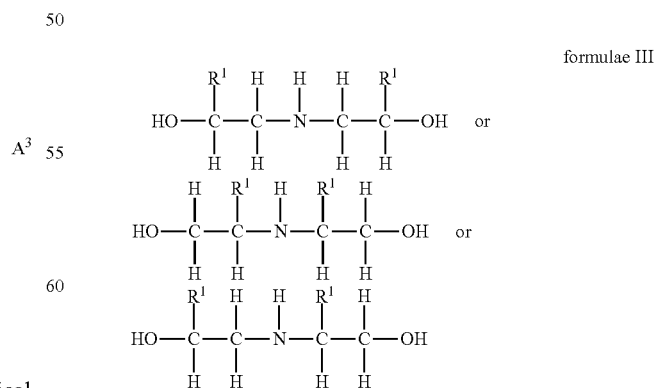

where radicals $R^1$ simultaneously or independently of one another are hydrogen, methyl, ethyl, propyl.

Particular preference is given in accordance with the invention to using the following compounds as starting materials for preparing the β-hydroxyalkylamides: diethanolamine (DEA), di-isopropanolamine (DIPA), di-sec-butanolamine, N-methylethanolamine, N-methylisopropanolamine.

Suitable starting compounds for the substituent A in the β-hydroxyalkylamides of the invention are 1,2-substituted, 1,3-substituted, and 1,4-substituted cyclohexanedicarboxylic acid derivatives, more particularly dialkyl esters of cyclohexanedicarboxylic acids. The starting compounds here may have any desired cis/trans content.

Preference is given to using compounds of the formula IV:

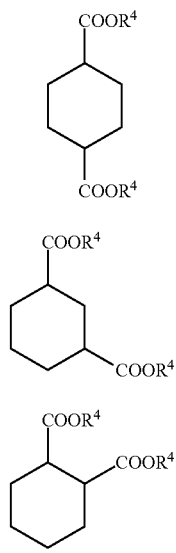

where radicals $R^4$ simultaneously or independently of one another are methyl, ethyl, propyl, butyl.

Particular preference is given to using 1,4-substituted cyclohexanedicarboxylic esters, very preferably dimethyl 1,4-cyclohexyldicarboxylate.

The β-hydroxyalkylamides that are particularly preferred in accordance with the invention, formed from dialkyl 1,4-cyclohexyldicarboxylates, preferably from dimethyl 1,4-cyclohexyldicarboxylate, have a trans content, based on the position of the carboxyl groups on the cyclohexyl ring, of greater than or equal to 70 mol %, preferably greater than 80 mol %, and more preferably of greater than 85 mol %. It is possible here to use dialkyl 1,4-cyclohexyldicarboxylates which have any desired trans content.

The β-hydroxyalkylamides (I) of the invention are present in solid form below 150° C., preferably below 170° C., more preferably below 180° C.

As byproducts the β-hydroxyalkylamides also contain, to a small extent, dimers, trimers, oligomers, and other condensation products of the target product.

Particularly preferred β-hydroxyalkylamides of the invention have the following formulae:

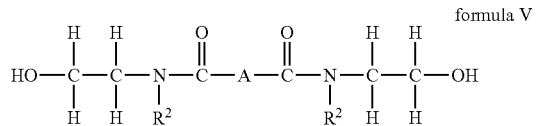
formula V

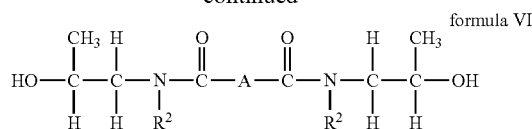
formula VI

formula VII

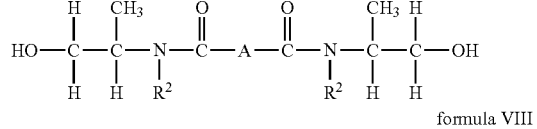
formula VIII

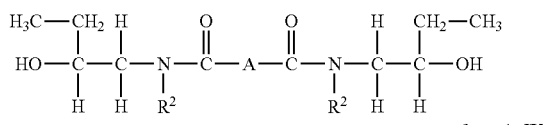
formula IX

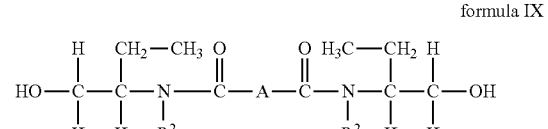
formula X

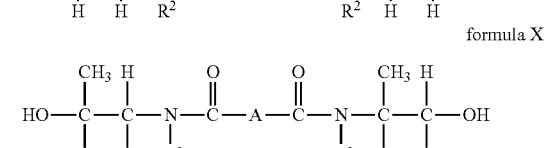
formula XI where
$R^2$ is methyl,
or

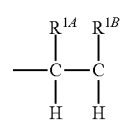

where $R^{1A}$ is hydrogen and $R^{1B}$ is methyl, ethyl, propyl,
or
$R^{1A}$ is methyl, ethyl, propyl and $R^{1B}$ is hydrogen;
and
A is a 1,4-disubstituted cyclohexane ring of the formula

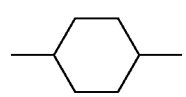

where the trans content of A is ≥70 mol %;
and where the β-hydroxyalkylamides are present in solid form below 150° C.

The β-hydroxyalkylamide which is particularly preferred in accordance with the invention, formed from dimethyl 1,4-cyclohexyldicarboxylate and diethanolamine, with four β-hydroxyalkylamide groups per molecule of the formula XII formula XII

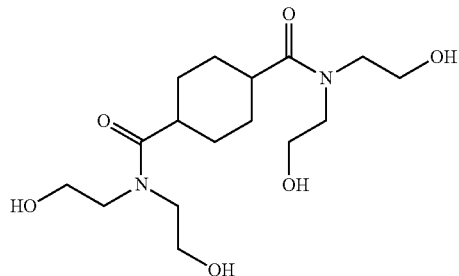

has a trans content on the cyclohexyl ring of greater than or equal to 70 mol %, preferably greater than 80 mol %, and more preferably of greater than 85 mol %.

The β-hydroxyalkylamides of the invention can be prepared in principle by known methods, as for example in accordance with DE 25 09 237, DE 198 23 925, EP 473 380, EP 960 878, WO 2000050384, WO 200055266. The method may be carried out continuously, semicontinuously or discontinuously, such as by a batch method, for example.

Preferred, however, is the continuous method, described in more detail below, for preparing the β-hydroxyalkylamides from dialkyl 1,4-cyclohexyldicarboxylates.

The invention also relates to a method for the solvent-free, continuous preparation of the preferred β-hydroxyalkylamides of the invention from dialkyl 1,4-cyclohexyldicarboxylates, more particularly from dimethyl 1,4-cyclohexyldicarboxylate, having a trans content on the cyclohexyl ring of greater than or equal to 70 mol %, preferably greater than 80 mol %, and more preferably of greater than 85 mol %, and present in solid form below 150° C., in an extruder, intensive compounder, intensive mixer or static mixer.

It has been found that an accumulation of the trans form to 70 mol % trans on the 1,4-disubstituted cyclohexane ring, or more, takes place, surprisingly, very simply in the preparation of the β-hydroxyalkylamides, by means of a continuous method in an extruder, intensive compounder, intensive mixer or static mixer. It is possible here to use dialkyl 1,4-cyclohexyldicarboxylates which have any desired trans content.

In the dialkyl 1,4-cyclohexyldicarboxylate starting product of the invention that is used, depending on the source of the raw material, the trans configuration is usually between 15 and 35 mol %. However, any desired isomer composition can be used.

The invention accordingly provides a method for the solvent-free and continuous preparation of β-hydroxyalkylamides having at least two or three or four β-hydroxyalkylamide groups per molecule of the formula I formula I

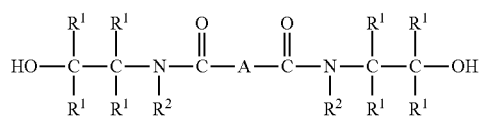

where
R¹ and R² independently of one another are identical or different radicals selected from alkyl radical, cycloalkyl radical, aryl radical, aralkyl radical or alkenyl radical having 1-24 carbon atoms, it also being possible for the radicals to contain heteroatoms and/or functional groups, and it also being possible for R¹ to be hydrogen, and it also being possible for R² to be

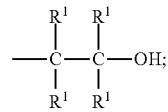

and
A is a 1,4-disubstituted cyclohexane ring of the formula

where the trans content of A is ≥70 mol %;
and
where the β-hydroxyalkylamides (I) are present in solid form below 150° C.,
in an extruder, intensive compounder, intensive mixer or static mixer.

The principle of the method is that the reaction of the reactants takes place continuously in an extruder, intensive compounder, intensive mixer or static mixer by intensive mixing and brief reaction, preferably with supply of heat.

In the method it is possible to employ temperatures of 50 to 325° C., with the temperature varying according to the product, as shown by the examples.

Intensive mixing and brief reaction with supply of heat means that the residence time of the reactants in the above-mentioned assemblies is typically 3 seconds to 15 minutes, preferably 3 seconds to 5 minutes, more preferably 5 to 180 seconds. During this time, the reactants are briefly brought to reaction with supply of heat at temperatures from 50° C. to 325° C., preferably from 50 to 225° C., very preferably from 70 to 200° C. Depending on the nature of the reactants and of the end products, however, these figures for residence time and temperature may also occupy other preferred ranges.

Optionally, a continuous after-reaction is added on.

The completeness of the reaction is ensured by removal of the alcohols formed in the amidation. This removal is accomplished preferably by the alcohol as being stripped off using reduced pressure via openings in the housings of the extruder or intensive compounder or intensive mixer or static mixer, and/or by passing a gas stream over the intensively combined reaction mixture, with the alcohols, which are more volatile, being carried out by the gas stream.

The reaction may be accelerated by catalysts. Suitability is possessed by hydroxides and/or alcoholates of alkali metals, such as sodium or potassium hydroxide, sodium or potassium methanolate, quaternary ammonium hydroxides, alkoxides and/or other strong bases. The concentration is 0.01% to 5%, preferably 0.1% to 3%, based on the total mass employed.

The arrangement of reduced-pressure domes and/or gas overpassage locations may be varied and is guided by the nature of the reactants and of the alcohols which are formed. Also possible is an additional location, located downstream of the actual reaction section, for the removal of residual amounts of alcohol.

Through subsequent rapid cooling the end product is then obtained.

Assemblies particularly suitable, and preferably used, for the method of the invention are extruders such as single-screw or multiscrew extruders, more particularly twin-screw extruders, planetary roller extruders or annular extruders, (flow tube, intensive compounders, intensive mixers, or static mixers). Particularly preferred are twin-screw or multiscrew extruders, more particularly twin-screw extruders.

It was surprising that the reaction, which in a continuous method takes several hours, proceeds completely within a few seconds in the stated assemblies, and, given suitable catalysis, that the conversion of the cis form to the trans form is also accomplished. A fundamental fact is that brief thermal exposure in conjunction with the mixing effect of the intensive compounder is sufficient for complete or very substantial reaction of the reactants. As a result of appropriate equipping of the mixing chambers and/or compilation of the screw geometries, the intensive compounders allow intensive, rapid mixing with intensive heat exchange at the same time. Moreover, a uniform flow in the longitudinal direction, with an extremely uniform residence time, is also ensured. Also possible must be different thermal conditioning in the individual barrels or sections of the apparatus.

The starting products are metered to the assemblies generally in separate product streams. When more than two product streams, they may also be supplied in bundled form. It is also possible to admix this product stream, additionally, with catalysts and/or adjuvants such as flow control agents, stabilizers or adhesion promoters. The streams may also be divided and thus supplied in different fractions at different locations to the assemblies. In this way, concentration gradients are set up in a specific way, allowing the reaction to be taken to completion. The entry location of the product streams can be variable in sequence and staggered in time.

For preliminary reaction and/or for completion of the reaction it is also possible for two or more assemblies to be combined.

The assemblies used for the reaction are equipped with reduced-pressure domes, for removal during the reaction of the alcohols formed during the reaction (depending on the carboxylic ester used). This measure serves for completion of the reaction, by shifting the chemical equilibrium in the direction of the desired β-hydroxyalkylamide.

Storage at temperatures above 40° C. for between 1 h and four weeks and/or by recrystallization of the product, may improve the product quality.

Final processing, depending on the viscosity of the product leaving the assembly or the after-reaction zone, is first brought to an appropriate temperature by further cooling using suitable appliances. This is followed by pelletizing or else by comminution to a desired particle size, using roll crushers, hammer mills, cutting mills, classifier mills, pinned-disk mills, flaking rolls or the like.

The invention also provides the use of the β-hydroxyalkylamides having two or three or four β-hydroxyalkylamide groups per molecule of the formula I

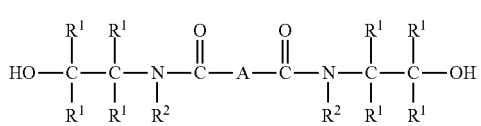

where
$R^1$ and $R^2$ independently of one another are identical or different radicals selected from alkyl radical, cycloalkyl radical, aryl radical, aralkyl radical or alkenyl radical having 1-24 carbon atoms, it also being possible for the radicals to contain heteroatoms and/or functional groups, and it also being possible for $R^1$ to be hydrogen, and it also being possible for $R^2$ to be

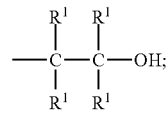

and
A is

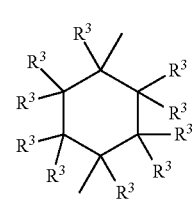

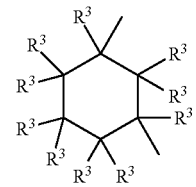

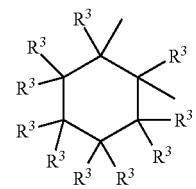

where radicals $R^3$ independently of one another are identical or different radicals selected from hydrogen, alkyl radical, cycloalkyl radical, aryl radical, aralkyl radical or alkenyl radical having 1-24 carbon atoms, it also being possible for the radicals to contain heteroatoms and/or functional groups, and it being possible for two or more substituents $R^3$ to be linked with one another to form rings;

where the β-hydroxyalkylamides are present in solid form below 150° C., as crosslinkers for polymers containing carboxyl groups, preferably for polyesters containing carboxyl groups.

The invention also provides the use of the β-hydroxyalkylamides of the invention in powder coating materials, preferably in carboxyl-containing polyester powder coating materials.

The invention also provides the use of the β-hydroxyalkylamides of the invention in powder coating materials which after curing have matt surfaces, with <50 gloss units, measured as reflectometer values according to DIN 67530/ISO 2813 at an incident angle of 60°.

Provided preferably by the invention is the compound N,N,N',N'-tetrakis(2-hydroxyethyl)cyclohexyl-1,4-diamide according to the formula XIIA

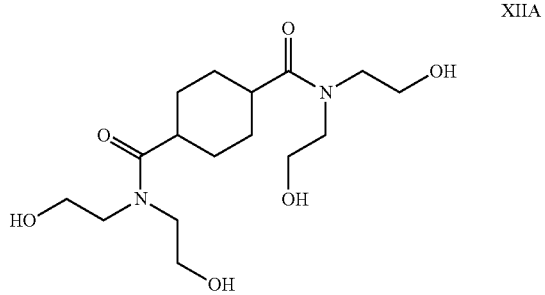 [SMILES: O=C(C1CCC(C(=O)N(CCO)CCO)CC1)N(CCO)CCO]

XIIA which has the following parameters:
1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

Provided more preferably by the invention is the β-hydroxyalkylamide N,N,N',N'-tetrakis(2-hydroxyethyl)cyclohexyl-1,4-diamide according to the formula XIIA, having a trans content on the cyclohexyl ring of greater than or equal to 70 mol %, preferably greater than 80 mol %, and more preferably of greater than 85 mol %, based on the total amount of all of the isomers of N,N,N',N'-tetrakis(2-hydroxyethyl)cyclohexyl-1,4-diamide that are present.

Additionally, this β-hydroxyalkylamide of the invention, N,N,N',N'-tetrakis(2-hydroxyethyl)cyclohexyl-1,4-diamide according to the formula XIIA, has two endothermic peaks by DSC analysis (differential scanning calorimetry): first a peak having a maximum (peak 1) of about 160° C., and a further, second peak having a maximum (peak 2) at about 190° C.—see the figures for the examples. Preferably, the first peak is located in the region of 140-170° C., with a maximum of 155-165° C., and the second peak is located in the region of 170-210° C., with a maximum of 175-207° C. More preferably, the first peak is located in the region of 155-170° C., with a maximum of 158-165° C., and the second peak is located in the region of 170-210° C., with a maximum of 180-205° C.

The ratio of the enthalpies of endothermic peak 1 (~160° C.) to endothermic peak 2 (~190° C.) may be 1:1 to 1:5, preferably 1:1 to 1:3.

The DSC measurements were carried out in accordance with DIN EN ISO 11357-1 from March 2010. A heat flow difference calorimeter from the manufacturer Mettler-Toledo, model DSC 821, was used. The samples are run once from −30° C. to 250° C. at 10 K/min.

The XRPD measurements on powder samples were carried out in an x-ray diffractometer using Cu Kα radiation (1.541 Å). In accordance with FIG. 9, the following significant and characteristic 6 peaks were found for the β-hydroxyalkylamide N,N,N',N'-tetrakis(2-hydroxyethyl)cyclohexyl-1,4-diamide according to the formula XIIA:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

Especially preferred is the β-hydroxyalkylamide N,N,N',N'-tetrakis(2-hydroxyethyl)cyclohexyl-1,4-diamide according to the formula XIIA having a trans content on the cyclohexyl ring of greater than or equal to 92 mol %, preferably greater than 94 mol %, and very preferably of greater than 96 mol %, and especially preferably of greater than 98 mol %, based on the total amount of all of the isomers of N,N,N',N'-tetrakis(2-hydroxyethyl)cyclohexyl-1,4-diamide that are present.

The β-hydroxyalkylamide of the invention, of the formula XIIA, is present in solid form below 175° C., preferably below 180° C., and more preferably of below 185° C.

The β-hydroxyalkylamide of the invention, of the formula XIIA, having features 1. to 4. was investigated by x-ray structural analysis of a single crystal. Comprehensive details relating to the measurement are summarized in annex 1. The x-ray structural analysis of a single crystal gave the following result for the structure:

| Crystal system: | Orthorhombic | |
|---|---|---|
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å$^3$ | |

The figures in the brackets indicate the measurement accuracy in plus and minus in each case for the corresponding last digit or last two digits.

The invention also provides the compound N,N,N',N'-tetrakis(2-hydroxyethyl)cyclohexyl-1,4-diamide according to the formula XIIA

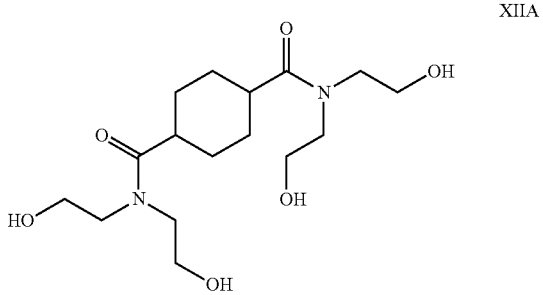 [SMILES: O=C(C1CCC(C(=O)N(CCO)CCO)CC1)N(CCO)CCO]

which has the following parameters:
1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

5. and which, according to x-ray structural analysis of a single crystal, has the following parameters:

| | | |
| --- | --- | --- |
| Crystal system: | Orthorhombic | |
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å$^3$ | |

Preparation

The particularly preferred N,N,N',N'-tetrakis(2-hydroxyethyl)cyclohexyl-1,4-diamide according to the formula XIIA is obtainable by various methods:

First of all, as described precisely earlier on above, the N,N,N',N'-tetrakis(2-hydroxyethyl)cyclohexyl-1,4-diamide according to the formula XIIA is prepared, preferably solventlessly, in an extruder, intensive compounder, intensive mixer or static mixer, preferably in an extruder. Temperatures of 100 to 180° C. are employed here. This is followed by recrystallization from a suitable solvent, preferably water. Following dissolution at temperatures of 20-100° C. and crystallization, the N,N,N',N'-tetrakis(2-hydroxyethyl)cyclohexyl-1,4-diamide according to the formula XIIA with the above-stated parameters is obtained. It can then, subsequently, be washed with alcohols, preferably methanol, and dried. Drying takes place preferably at temperatures of 20-90° C., and may also take place under reduced pressure.

A further variant of the preparation takes place as described precisely earlier on above, by the N,N,N',N'-tetrakis(2-hydroxyethyl)cyclohexyl-1,4-diamide according to the formula XIIA being prepared, preferably solventlessly, in an extruder, intensive compounder, intensive mixer or static mixer, preferably in an extruder. In this case, temperatures of 100 to 180° C. are employed. This is followed by thermal conditioning at temperatures of 50-100° C., preferably at temperatures of 70-85° C. The time is more than 6 hours, preferably more than 12 hours. Thermal conditioning may take place under reduced pressure.

Also provided by the invention, accordingly, is a method for the solvent-free, continuous preparation of N,N,N',N'-tetrakis(2-hydroxyethyl)cyclohexyl-1,4-diamide according to the formula XIIA from dimethyl 1,4-cyclohexyldicarboxylate and diethanolamine, having four β-hydroxyalkylamide groups per molecule, which has the following parameters:
1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | in an extruder, intensive compounder, intensive mixer or static mixer;
a) and recrystallization
b) or thermal conditioning at temperatures of 50-100° C., the time being more than 6 hours,
of the resultant product.

The particularly preferred N,N,N',N'-tetrakis(2-hydroxyethyl)cyclohexyl-1,4-diamide according to the formula XIIA may also take place discontinuously in solvent, in other words in a batch method.

The reaction is carried out in customary reactors. Operation here may be unpressurized, using a reflux condenser, or under pressure, with a closed reactor.

The synthesis is carried out in a solvent, preferably in alcohols, preferably methanol. The amount of solvent added is greater than 10% by weight, preferably greater than 15% by weight, based on the total amount of all of the reactants (starting materials) employed. It is possible here to operate under reflux, or else at lower temperatures, and also higher temperatures, under pressure. Preparation takes place at temperatures of 20 to 120° C., preferably at 60 to 90° C., more preferably at 70 to 85° C. Crystallization gives the N,N,N',N'-tetrakis(2-hydroxyethyl)cyclohexyl-1,4-diamide according to the formula XIIA having the parameters stated above.

The invention also relates to a method for the discontinuous preparation of N,N,N',N'-tetrakis(2-hydroxyethyl)cyclohexyl-1,4-diamide according to the formula XIIA from dimethyl 1,4-cyclohexyldicarboxylate and diethanolamine, having four β-hydroxyalkylamide groups per molecule, which has the following parameters:

1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | in solvent.

The preparation of the N,N,N',N'-tetrakis(2-hydroxyethyl)cyclohexyl-1,4-diamide according to the formula XIIA may also take place in closed apparatus under pressure at temperatures of 60 to 140° C., without addition of solvents, and this is likewise provided by the invention.

The N,N,N',N'-tetrakis(2-hydroxyethyl)cyclohexyl-1,4-diamide according to the formula XIIA that is thus prepared in a batch method can be recrystallized from suitable solvents, preferably from water or alcohols, preferably from methanol.

Moreover, the preparation of the N,N,N',N'-tetrakis(2-hydroxyethyl)cyclohexyl-1,4-diamide according to the formula XIIA may also take place discontinuously without solvents.

The reaction is carried out in customary reactors. It is possible here to operate using a reflux condenser. The preparation takes place preferably at temperatures of 20 to 140° C., preferably 60 to 90° C., more preferably at 70 to 85° C. The 11-hydroxyalkylamide obtained thus in a batch method is then recrystallized from suitable solvents, preferably from water or alcohols, preferably from methanol. Crystallization gives the N,N,N',N'-tetrakis(2-hydroxyethyl)cyclohexyl-1,4-diamide according to the formula XIIA with the parameters specified above. This method is likewise provided by the invention.

The concentration of all of the isomers of N,N,N',N'-tetrakis(2-hydroxyethyl)cyclohexyl-1,4-diamide in the end product after its preparation is 75% by mass, preferably 80% by mass, and more preferably 85% by mass.

Figure 2:
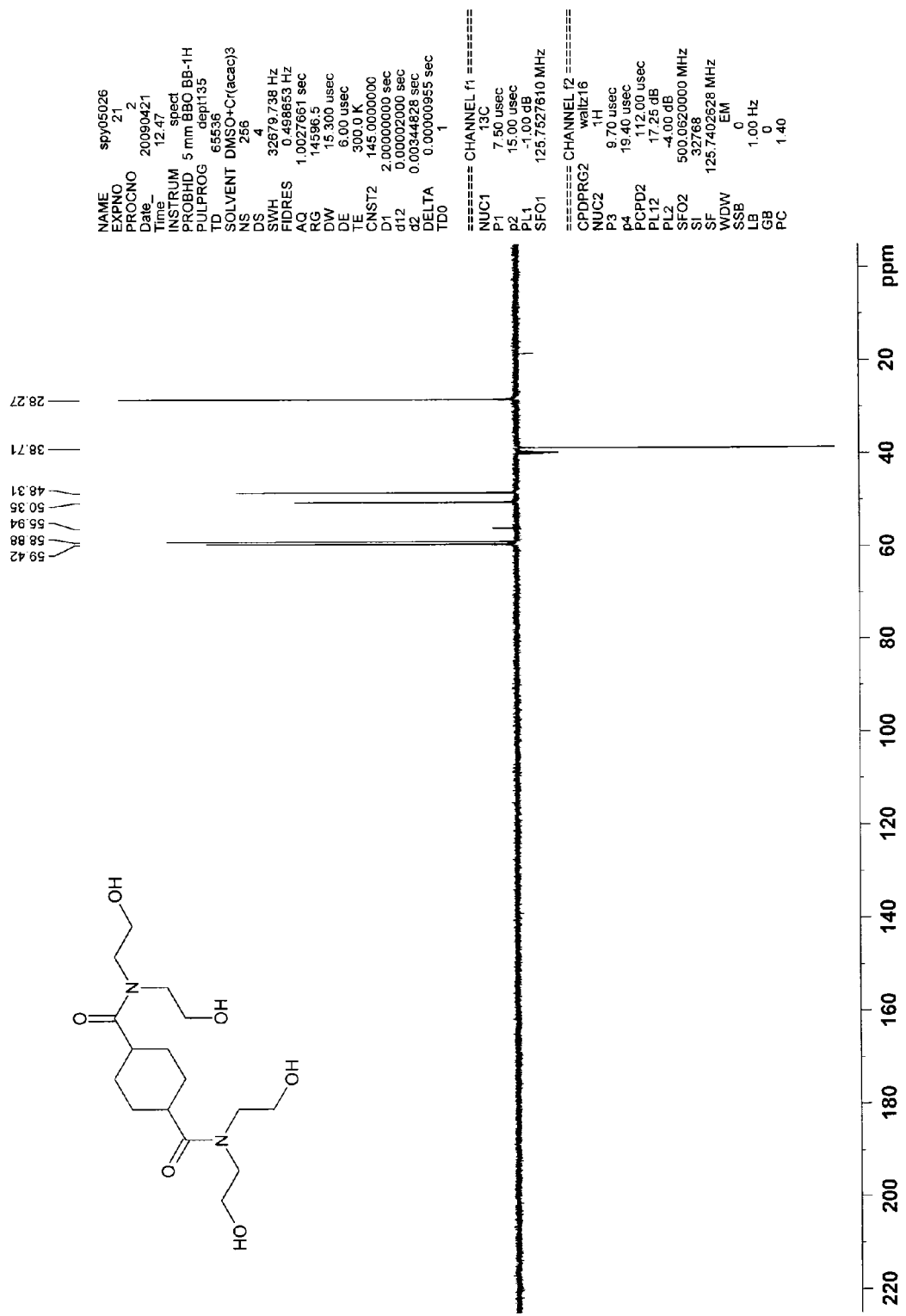
FIG. 2 is a $^{13}$C-NMR spectrum of the trans-N,N,N',N'-tetrakis(2-hydroxyethyl)cyclohexyl-1,4-diamide of formula XII.
Figure 3:
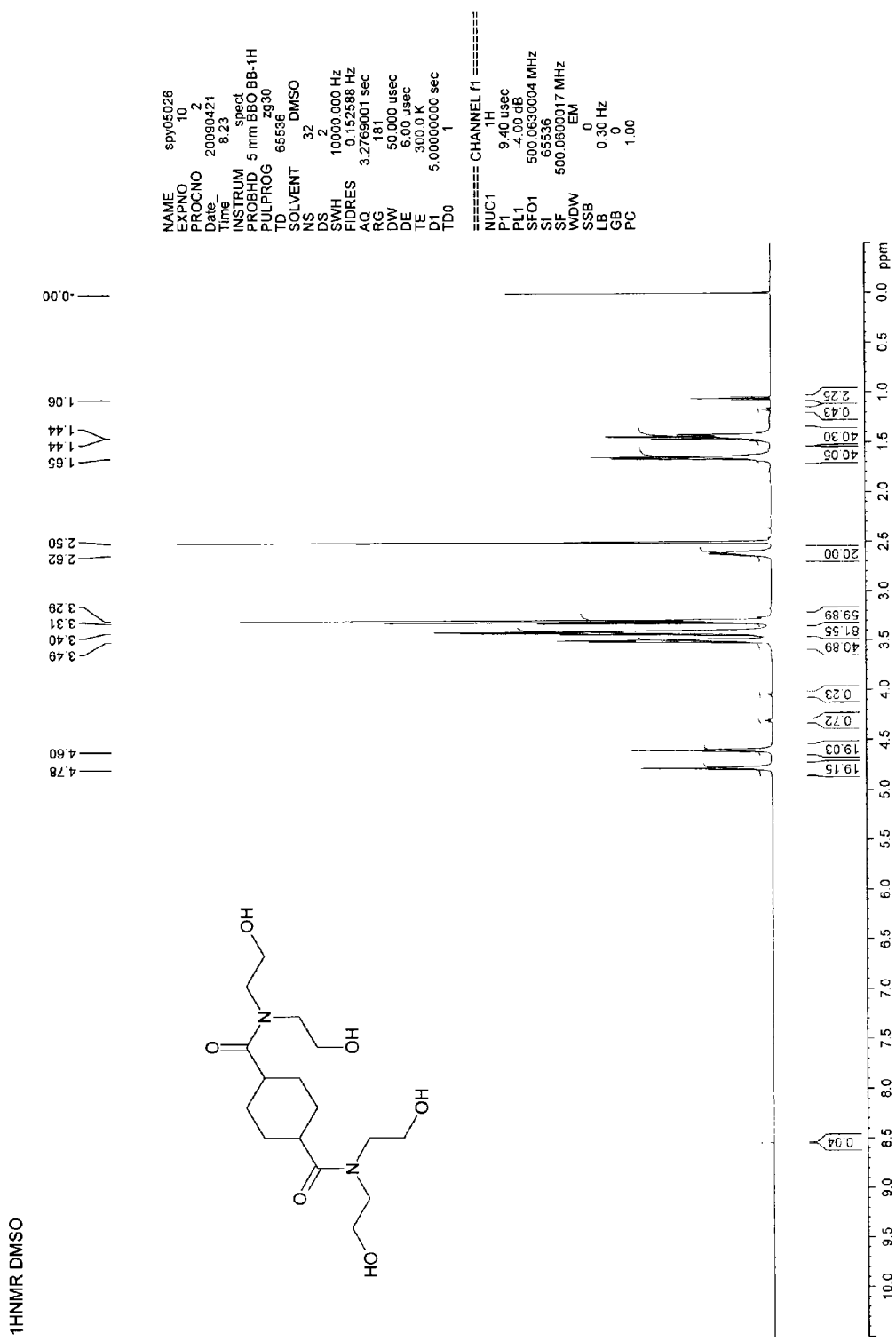
FIG. 3 is a H-NMR spectrum of the trans-N,N,N',N'-tetrakis(2-hydroxyethyl)cyclohexyl-1,4-diamide of formula XII.
Figure 4:
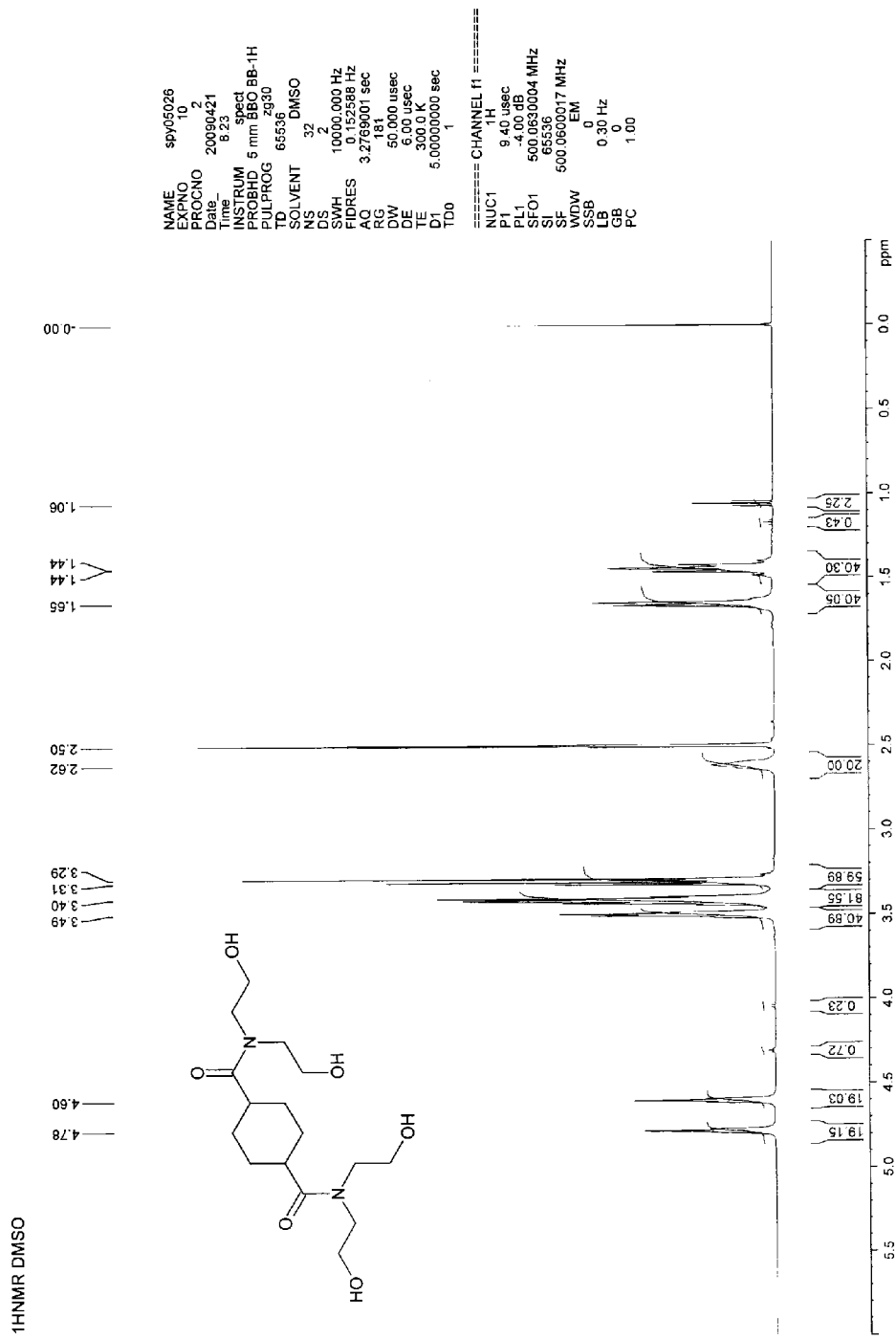
FIG. 4 is a H-NMR spectrum of the trans-N,N,N',N'-tetrakis(2-hydroxyethyl)cyclohexyl-1,4-diamide of formula XII.

This β-hydroxyalkylamide as described and characterized here, N,N,N',N'-tetrakis(2-hydroxyethyl)cyclohexyl-1,4-diamide of the formula XIIA, produces far-reaching matting in powder coating materials, with a gloss of less than 50 scale divisions at the 60° angle, as has been shown in the examples. This product of the formula XIIA therefore differs clearly from the disclosed β-hydroxyalkylamide according to laid-open specification KR 10-2009-0111720 (and that from β-hydroxyalkylamide Korean Ind. Eng. Chem., vol. 20, No. 2, April 2009, 195-200), as demonstrated there in FIG. 2 on page 15, having only one peak, according to DSC analysis, at about 190° C., and, as shown by comparative example 4c, not leading to coatings having matt surfaces.

The invention also provides the use of N,N,N',N'-tetrakis(2-hydroxyethyl)cyclohexyl-1,4-diamide according to the formula XIIA

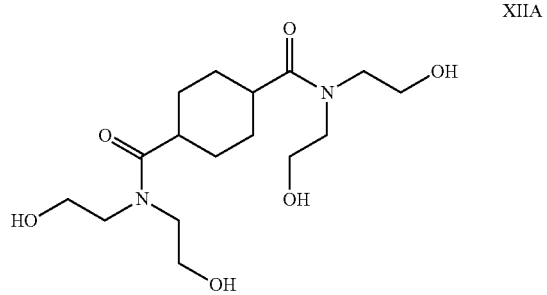 [SMILES: O=C(C1CCC(C(=O)N(CCO)CCO)CC1)N(CCO)CCO]

which has the following parameters:

1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
| --- | --- | --- |
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 | for producing coatings having matt surfaces, more particularly in powder coating materials, preferably in carboxyl-containing polyester powder coating materials.

The invention also provides the use of N,N,N',N'-tetrakis(2-hydroxyethyl)cyclohexyl-1,4-diamide according to the formula XIIA for producing coatings having matt surfaces with <50 gloss units, measured as reflectometer values according to DIN 67530/ISO 2813 at an incident angle of 60°.

The invention also provides the use of N,N,N',N'-tetrakis (2-hydroxyethyl)cyclohexyl-1,4-diamide according to the formula XIIA

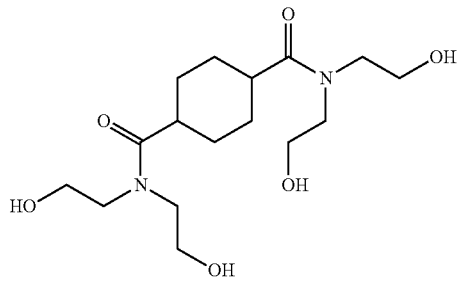

XIIA which has the following parameters:

1. a trans content on the cyclohexyl ring of greater than or equal to 70 mol %, based on the total amount of all of the isomers of N,N,N',N'-tetrakis(2-hydroxyethyl)cyclohexyl-1,4-diamide that are present, and
2. two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C., and
3. the ratio of the enthalpies of endothermic peak 1 to endothermic peak 2 is 1:1 to 1:5, and
4. the XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

5. and which, according to x-ray structural analysis of a single crystal, has the following parameters:

| | | |
|---|---|---|
| Crystal system: | Orthorhombic | |
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å³ | |

The subject matter of the invention is illustrated below by means of examples.

EXAMPLES

Example 1

Preparation of a β-hydroxyalkylamide from dimethyl 1,4-cyclohexyldicarboxylate and diethanolamine by the method of the invention

| Substances employed | Product description, manufacturer |
|---|---|
| Diethanolamine (DEA) | Dow Chemical |
| Dimethyl 1,4-cyclohexyldicarboxylate (DMCD) trans content 15-35 mol % | Dimethyl ester of 1,4-cyclohexanedicarboxylic acid, EASTMAN |
| Sodium methylate | 30% strength in methanol |

Three streams were operated:
Stream 1 consisted of DMCD
Stream 2 consisted of DEA
Stream 3 consisted of the catalyst, the methanolic sodium methylate solution.

The streams were metered such that the molar ratio between dimethyl 1,4-cyclohexyldicarboxylate and diethanolamine was 1:1.95.

The total amount of catalyst (only sodium methylate, calculated on solvent-free bases), based on the overall formula, was 0.50 to 3.0%.

Stream 1 was fed in at a rate of 10.0 kg/h into the first barrel of a twin-screw extruder (ZSK 30, 32 d) (stream temperature 80 to 130° C.).

Stream 2 was fed in at a rate of 9.9 kg/h (stream temperature 65 to 145° C.).

Stream 3 was introduced through nozzles from entry into the extruder in stream 2 (0.5 to 2.0 kg/h).

The extruder used consisted of 8 barrels, which were separately heatable and coolable. Barrels 1-5: 160° C., barrels 6-8: 120-160° C.

Barrels 3, 5, and 8 were provided with a reduced-pressure dome (100 to 600 mbar).

The extruder screws were fitted with conveying elements. Ahead of the reduced-pressure domes, kneading blocks were installed.

All temperatures represented setpoint temperatures. Regulation took place via electrical heating or water cooling. The extruder head was likewise heated electrically (100-160° C.).

The screw speed was 300 rpm. The reaction product was conveyed out of the extruder via a gear pump. The overall throughput was 20 kg/h.

The end product was cooled via a pipe section and/or via an extruder, and was guided onto a cooling belt, and cooled further. The product was subsequently recrystallized from deionized water at 100° C. and cooled to room temperature. The mother liquor was filtered off and the filtercake was subsequently washed three times in methanol at room temperature and then dried in a vacuum drying oven at 50° C. and about 20 mbar. It was subsequently ground.

TABLE 1

End products and characterization

| Product - Example | | 1 |
|---|---|---|
| Preparation | | Recrystallized |
| Trans-N,N,N',N'-tetrakis(2-hydroxyethyl)cyclohexyl-1,4-diamide[1] | % by mass | 95.30 |
| Cis-N,N,N',N'-tetrakis(2-hydroxyethyl)cyclohexyl-1,4-diamide[1] | % by mass | 0.28 |
| Σ N,N,N',N'-tetrakis(2-hydroxyethyl)cyclohexyl-1,4-diamide[1] | % by mass | 95.58 |
| DEA[1] | % by mass | 0.18 |
| OH number | mg KOH/g | 616 |
| Base number | mg KOH/g | 3 |
| Melting range | ° C. | 194-201 |

[1]Analytical values by GC
OH number: DIN 53240
Base number: DIN 53176
Melting range: DIN EN ISO 3146

The trans-N,N,N',N'-tetrakis(2-hydroxyethyl)cyclohexyl-1,4-diamide prepared (formula XII) was characterized by the NMR spectra of FIGS. 1-4.

Example 2

Powder Coating Material and Coating

The powder coating material with the inventive β-hydroxyalkylamide (matt curing agent) from example 1 was prepared in the melt by joint extrusion of all of the components as per table 2 at a temperature (barrel) of 90° C. (approximately 130° C. melt temperature). The composition of the raw materials is set out in table 2. The ratio of acid groups in the polyester to OH groups in the curing agent was 1:1.

The extrudate is subsequently cooled, ground and sieved to a particle size of <100 μm. The powder coating material thus prepared was applied using an electrostatic powder spraying unit at 60 KV to degreased steel panels (deep-drawn steel from Kruppel 210×70×0.8 mm) and/or aluminum panels (Q-panel AL-36 5005 H 14/08 0.8 mm) and baked in a forced-air drying oven between 160 to 220° C. The cured coating films have a film thickness of about 65 μm. The example data are based on a baking time of 20 minutes at 200° C.

Substances used:
1) Crosslinker:
   Inventive 1'-hydroxyalkylamide crosslinker according to example 1.
2) Amorphous polyester:
   CRYLCOAT® 2617-3, AN number: 32.7 mg KOH/g, Tg: 61° C., (Cytec Inc., USA)
3) Other Formulating Ingredients:
   Titanium dioxide KRONOS® 2160, (Kronos GmbH, D),
   RESIFLOW® PV 88, (Worlée-Chemie GmbH, D),
   Benzoin, (Merck-Schuchard OHG, D)

TABLE 2

| Product | % by mass | Substances used |
|---|---|---|
| HAA crosslinker | 3.00 | β-Hydroxyalkylamide example 1 |
| Amorphous polyester | 60.70 | CRYLCOAT ® 2617-3 |
| Pigment TiO2 | 35.00 | KRONOS ® 2160 |
| Flow control agent | 1.00 | RESIFLOW ® PV 88 |
| Degassing agent | 0.30 | Benzoin |
| Total | 100.00 | |

Properties of the Coating:
Baking conditions: 20 min at 200° C.
Gloss: 33 scale divisions at 60° angle
Gloss: 42 scale divisions at 85° angle
Erichsen cupping: >8 mm
Ball impact (direct): >80 in lb
Gloss: DIN 67530/ISO 2813
Erichsen cupping: DIN ISO 1520
Ball impact: DIN EN ISO 6272

The DSC Measurements

The DSC measurements were carried out in accordance with DIN EN ISO 11357-1 from March 2010.

A heat flow difference calorimeter from the manufacturer Mettler-Toledo model DSC 821, with the serial number 5116131417 was used. The samples are run once from −30° C. to 250° C. at 10 K/min.

Comprehensive Description of the Measurement Method:
1. type (heat flow difference calorimeter or power-compensated calorimeter), model and manufacturer of the DSC instrument used;
2. material, nature and type, and, where necessary, mass of the crucible used;
3. nature, purity, and volume flow rate of the flushing gas used;
4. nature of calibration method and details of the calibrating substances used, including source, mass, and other properties important for calibration;
5. details relating to sampling, sample preparation, and conditioning 1: Heat flow difference calorimeter
   Manufacturer: Mettler-Toledo
   Model: DSC 821
   Serial number: 5116131417
2: Crucible material: ultrapure aluminum
   Size: 40 μl, without pin,
   Mettler order No.: ME-26763
   Mass incl. lid: about 48 mg
3: Flushing gas: nitrogen
   Purity: 5.0 (>99.999% by volume)
   Volume flow rate: 40 ml/min
4: Calibration method: single
   Material 1: indium
   Mettler calibrating set ME-51119991
   Mass: about 6 mg per weighing
   Calibration of temperature (onset) and heat flow
   Material 2: deionized water
   Taken from the in-house system
   Mass: about 1 mg per weighing
   Calibration of temperature (onset)
5: Sampling: from sample vials supplied
   Sample mass: 8 to 10 mg
   Sample preparation: pressed on the crucible base using a die
   Crucible lid: perforated
   Measurement program: −30 to 250° C. 10 K/min 1×

Description of the XRPD Measurement:

The powder sample is pressed into a powder holder and measured in the Philips x-ray diffractometer PW1800 using Cu Kα radiation (1.541 Å) under the following conditions:
Excitation: 40 kV, 45 mA
Measuring range: 3°≤2θ≤40°
Step size: 0.1° (2Theta)
Time per step: 20 s
Rotation: ¼ revolution/sec
Receiving slit: coarse
Divergence slit: automatic Examples 3-4

| Substances employed | Product description, manufacturer |
|---|---|
| Diethanolamine (DEA) | Dow Chemical |
| Dimethyl 1,4-cyclohexyldicarboxylate (DMCD) (distilled) trans content 15-35 mol % | Dimethyl ester of 1,4-cyclohexanedicarboxylic acid, EASTMAN |
| Sodium methylate | 30% strength in methanol |

Example 3a

A three-neck flask with reflux condenser and glass stirrer is charged with 92.24 g of dimethyl 1,4-cyclohexyldicarboxylate with 96.91 g of diethanolamine, 10.84 g of 30% strength sodium methylate in methanol, and 52 g of methanol. A homogeneous solution is formed.

The batch is boiled for six hours under reflux with stirring in an oil heating bath (bath temperature 80° C.). Product begins to precipitate after about 0.5 hour.

The reaction batch is left to cool, and further product crystallizes. The precipitated product is subsequently separated from the methanol by filtration and then dried. The yield is more than 80% of theory. Table 3

Figure 5:
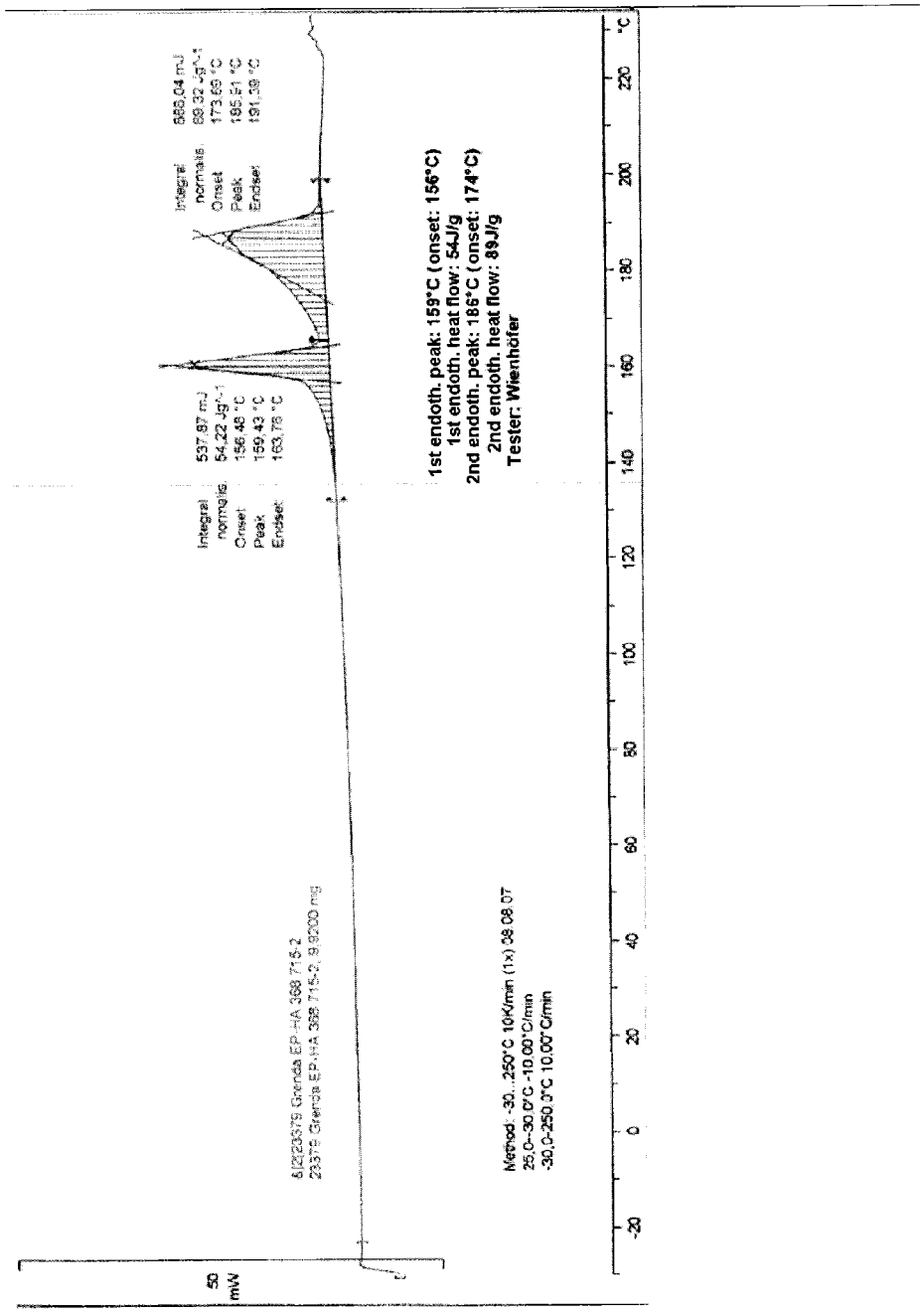
Figure 9:
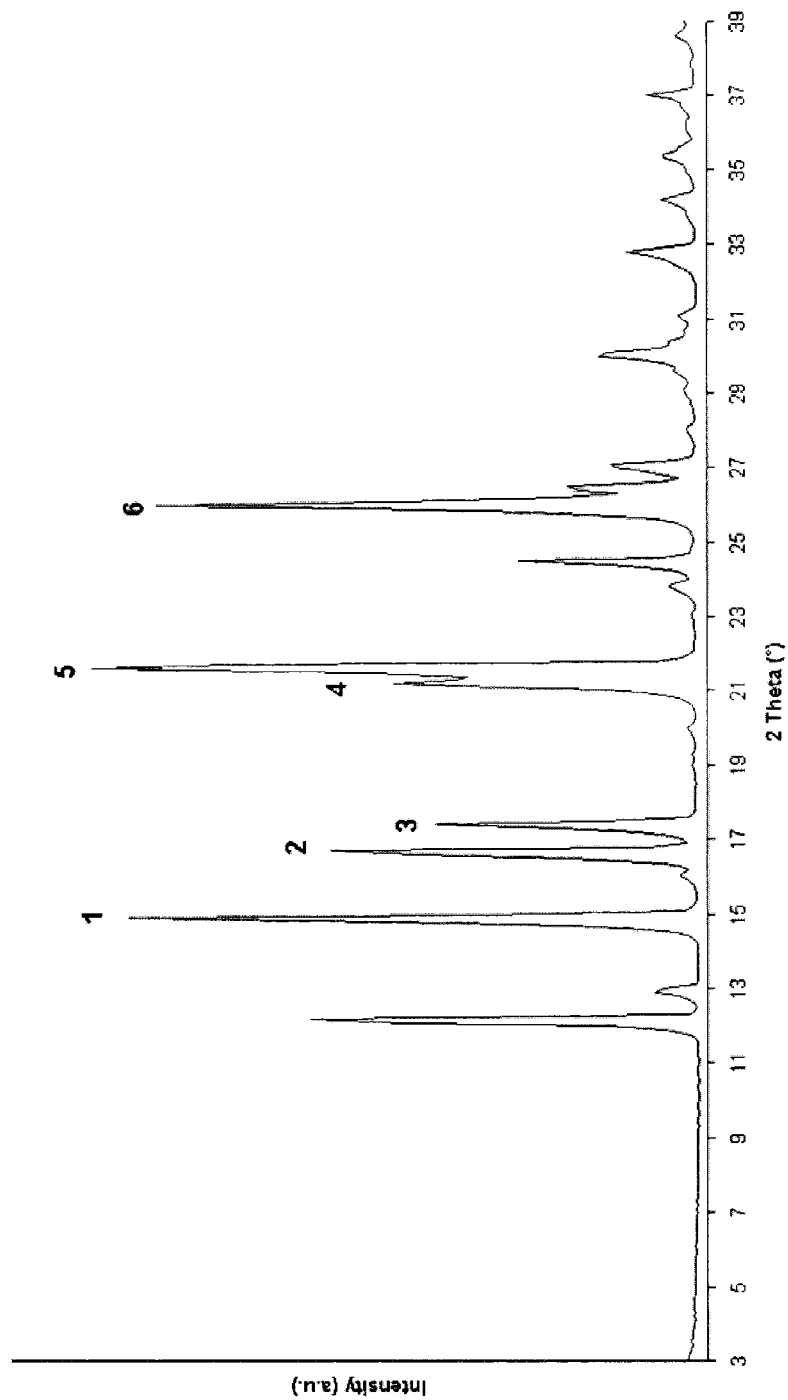
FIG. 9 is a XRPD (x-ray powder diffraction) analysis of the β-hydroxyalkylamide of the formula XIIA described in example 3a (matting material).

This gives, then, an N,N,N',N'-tetrakis(2-hydroxyethyl)cyclohexyl-1,4-diamide according to formula XIIA having two endothermic peaks ($1^{st}$ at about 160° C. and $2^{nd}$ at about 190° C.) in the DSC as per FIG. 5 and the XRPD spectrum as per FIG. 9 and table 5. This product thus produced produces far-reaching matting in powder coating materials, with a gloss of less than 50 scale divisions at the 60° angle, table 3.

Example 3b

The product produced in 3a is dissolved in boiling water, then slowly cooled down again; after crystallization has taken place, the crystallized product is briefly washed with methanol. Table 3

Figure 6:
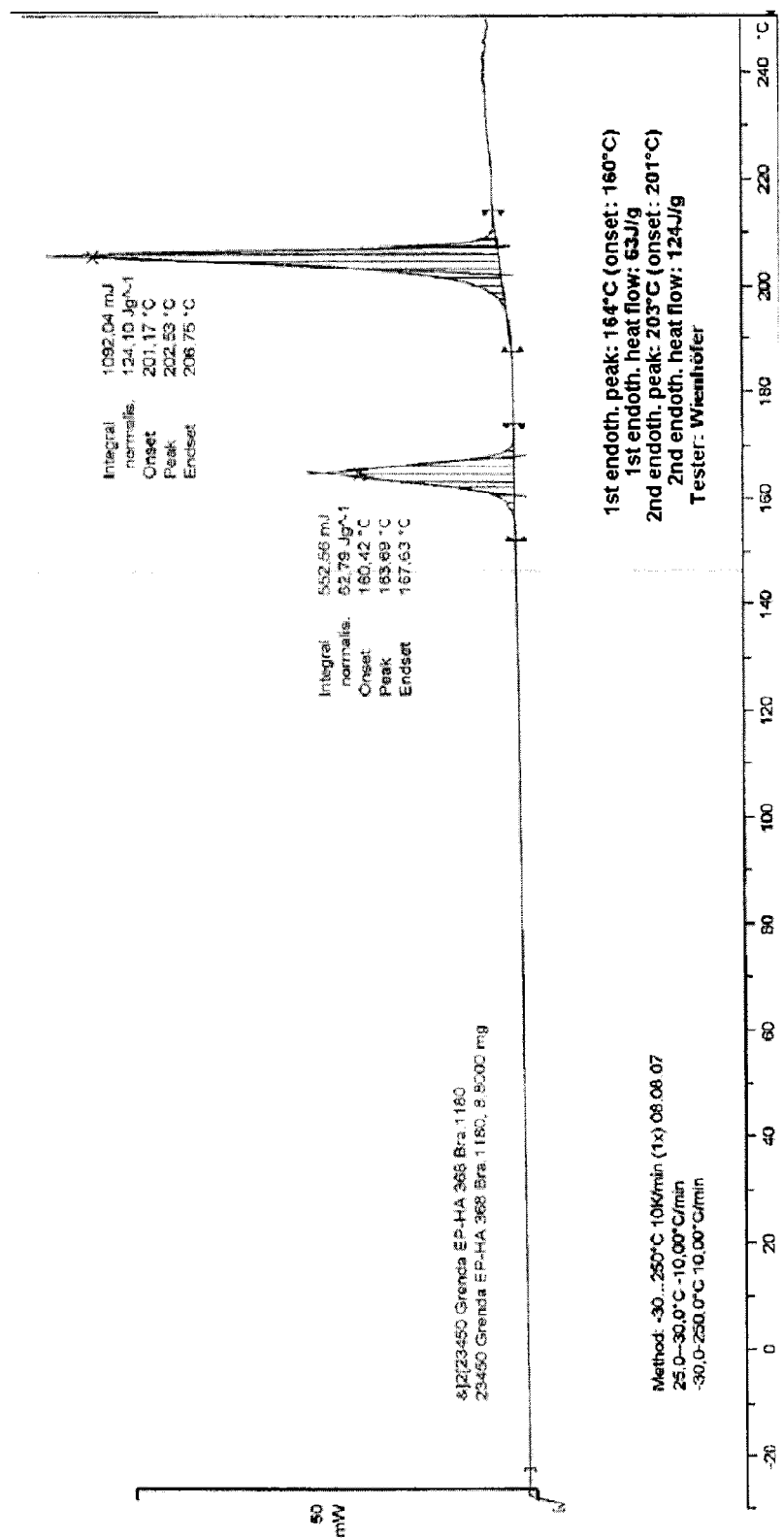
FIG. 6 is a DSC diagram of the β-hydroxyalkylamide of the formula XIIA described in example 3b.

This product shows the two endothermic peaks—see FIG. 6—with a matting effect present in the resulting powder coatings, of 29 scale divisions at the 60 degree angle, table 3.

TABLE 3

End products from discontinuous preparation examples 3a-3b and characterization thereof by GC analysis [1)]

| Example | | 3a | 3b |
|---|---|---|---|
| Starting material | | — | 3a |
| Preparation | | Batch preparation as described in example 3a | Boil 3a in deionized water cool slowly crystallize wash with methanol dry under reduced pressure |
| [1)] DEA | % by mass | 1.22 | <0.1 |
| [1)] Trans-N,N,N',N'-tetrakis(2-hydroxyethyl)cyclohexyl-1,4-diamide | % by mass | 89.34 | 91.81 |
| [1)] Cis-N,N,N',N'-tetrakis(2-hydroxyethyl)cyclohexyl-1,4-diamide | % by mass | 0.74 | 0.00 |
| Σ N,N,N',N'-tetrakis(2-hydroxyethyl)cyclohexyl-1,4-diamide | % by mass | 90.08 | 91.81 |
| Ratio of [1)] trans-N,N,N',N'-tetrakis(2-hydroxyethyl)cyclohexyl-1,4-diamide | mol % | 99.2 | 100.0 |
| to [1)] cis-N,N,N',N'-tetrakis(2-hydroxyethyl)cyclohexyl-1,4-diamide | mol % | 0.8 | 0.0 |
| OH number | mg KOH/g | 629 | — |
| Base number | | 22 | — |
| DSC: $1^{st}$ endo. peak - Δ H | ° C. - J/g | 159 - 24 | 164 - 63 |
| DSC: $2^{nd}$ endo. peak - Δ H | ° C. - J/g | 186 - 89 | 203 - 124 |

| Powder coating data | | | |
|---|---|---|---|
| PC experiment number | | 3a | 3b |
| HAA crosslinker | % by mass | 3.00 | 3.00 |
| CRYLCOAT ® 2617-3 | % by mass | 60.70 | 60.70 |
| KRONOS ® 2160 | % by mass | 35.00 | 35.00 |
| RESIFLOW ® PV 88 | % by mass | 1.00 | 1.00 |
| Benzoin | % by mass | 0.30 | 0.30 |
| Total | % by mass | 100.00 | 100.00 |
| Curing | min@ ° C. | 30 @ 200 | 30 @ 200 |
| Film thickness | μm | 64-70 | 70-73 |
| Gloss at 60° ∡ | Sc. div. | 30 | 29 |

[1)] Analytical values by GC
GC after silylation with Silyl 991 (BSTFA-TMCS 99:1) from Macherey und Nagel order No. 701.490.150. Silylation: 1 ml Silyl 991, 1 ml of pyridine, 35 mg of reaction product, 35 mg of C-18 hydrocarbon as internal standard, heat for 30 minutes at 80° C. in a closed ampoule.
OH number: DIN 53240
Base number: DIN 53176

Example 4a and 4b

4a

An N,N,N',N'-tetrakis(2-hydroxyethyl)cyclohexyl-1,4-diamide with the product data 4a is prepared in the same way as described in example 1 in an extruder (Werner und Pfleiderer ZSK 30, 32 d). Table 4

4b

This product, as prepared and described in example 4a, is recrystallized. For this purpose, the product from example 4a is dissolved with boiling in deionized water and then slowly cooled and crystallized, to convert it back into the solid form. It is subsequently washed with methanol and dried in a vacuum drying oven at 50° C. and about 20 mbar. Table 4

Figure 7:
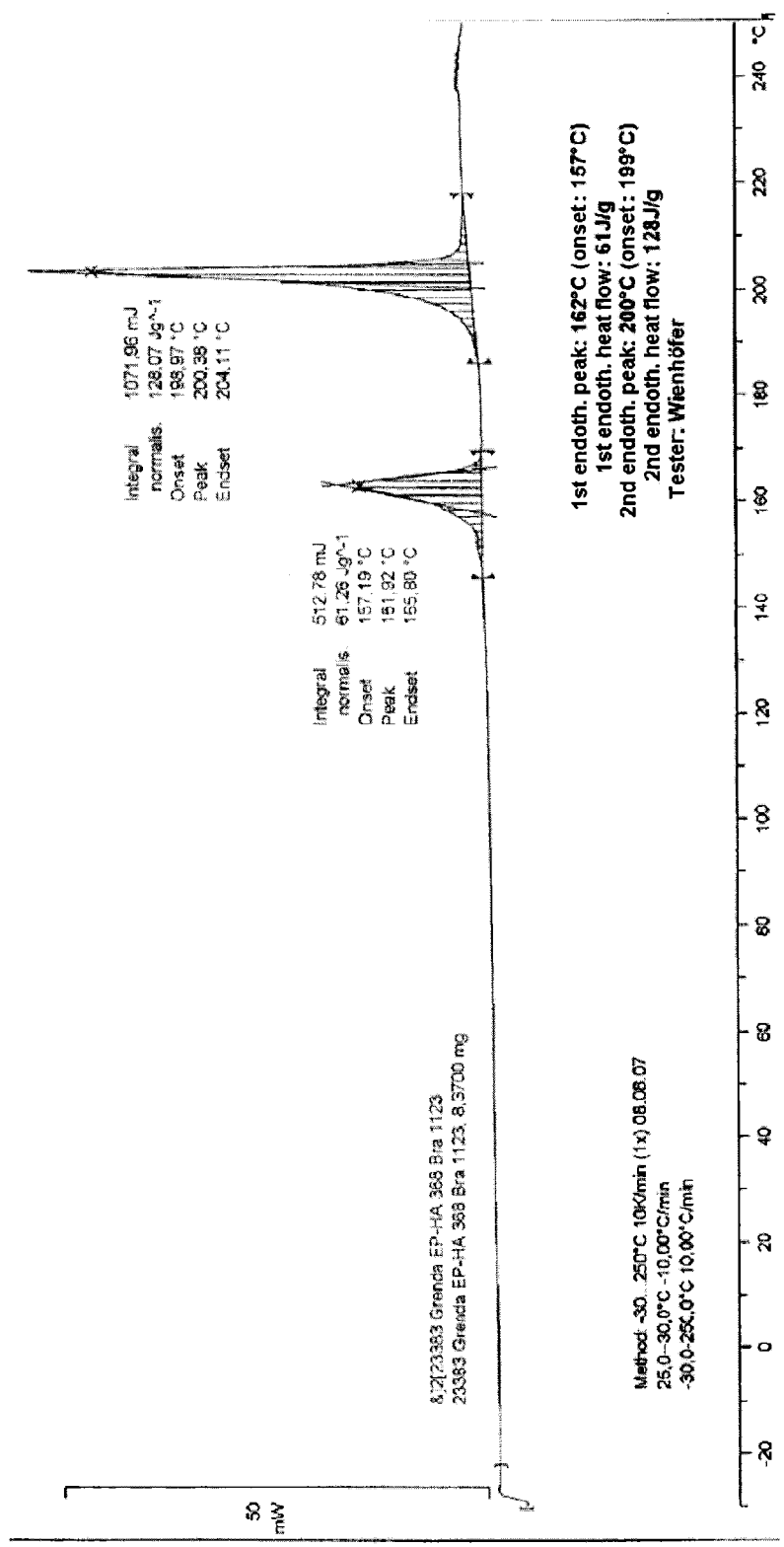
FIG. 7 is a DSC diagram of the β-hydroxyalkylamide of the formula XIIA described in example 4b.
Figure 11:
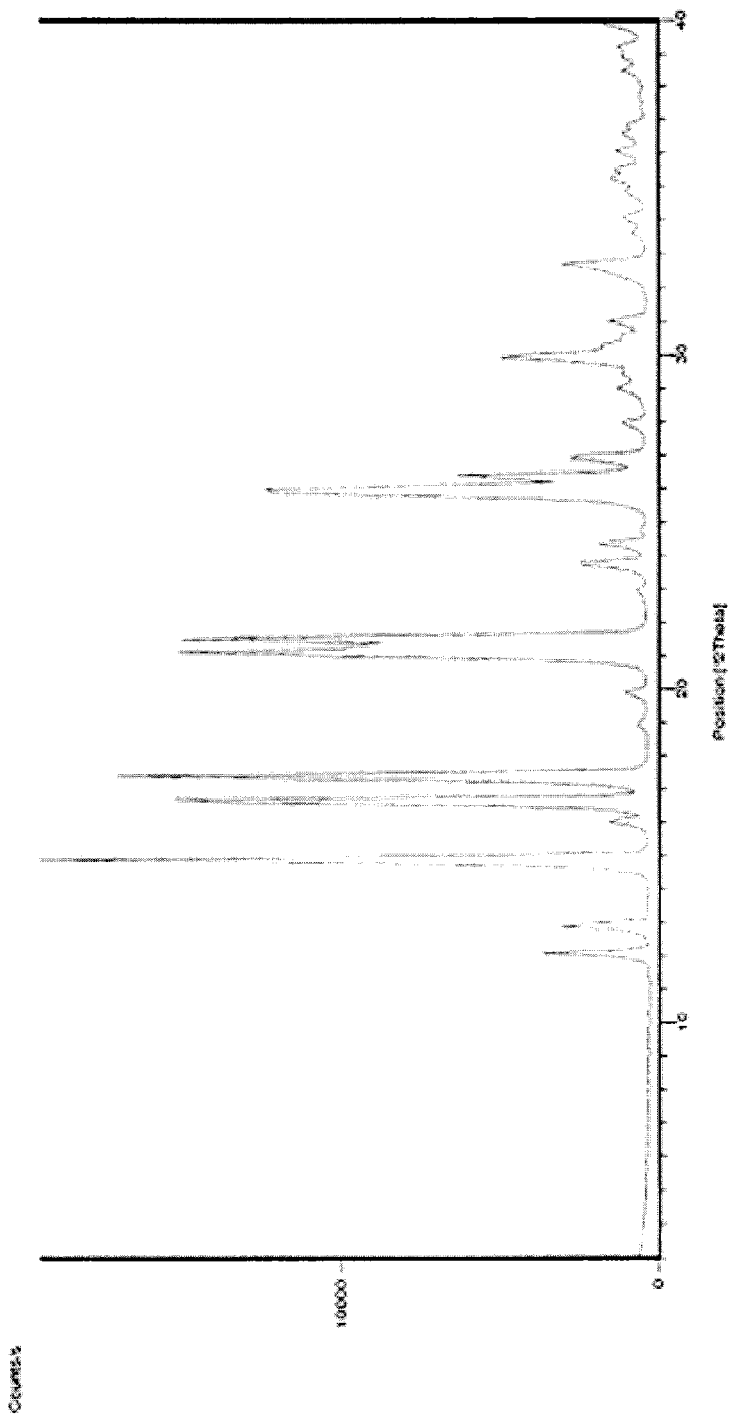
FIG. 11 is a XRPD (x-ray powder diffraction) analysis of the β-hydroxyalkylamide of the formula XIIA described in example 4b (matting material).

This, then, gives an N,N,N',N'-tetrakis(2-hydroxyethyl)cyclohexyl-1,4-diamide having two endothermic peaks ($1^{st}$ at about 160° C. and $2^{nd}$ at about 190° C.) in the DSC. This product with the two peaks in the DSC as per FIG. 7 and the XRPD spectrum as per FIG. 11 produces far-reaching matting in powder coating materials, with a gloss of 30 scale divisions at the 60° angle. Table 4

Comparative Example 4c

Figure 8:
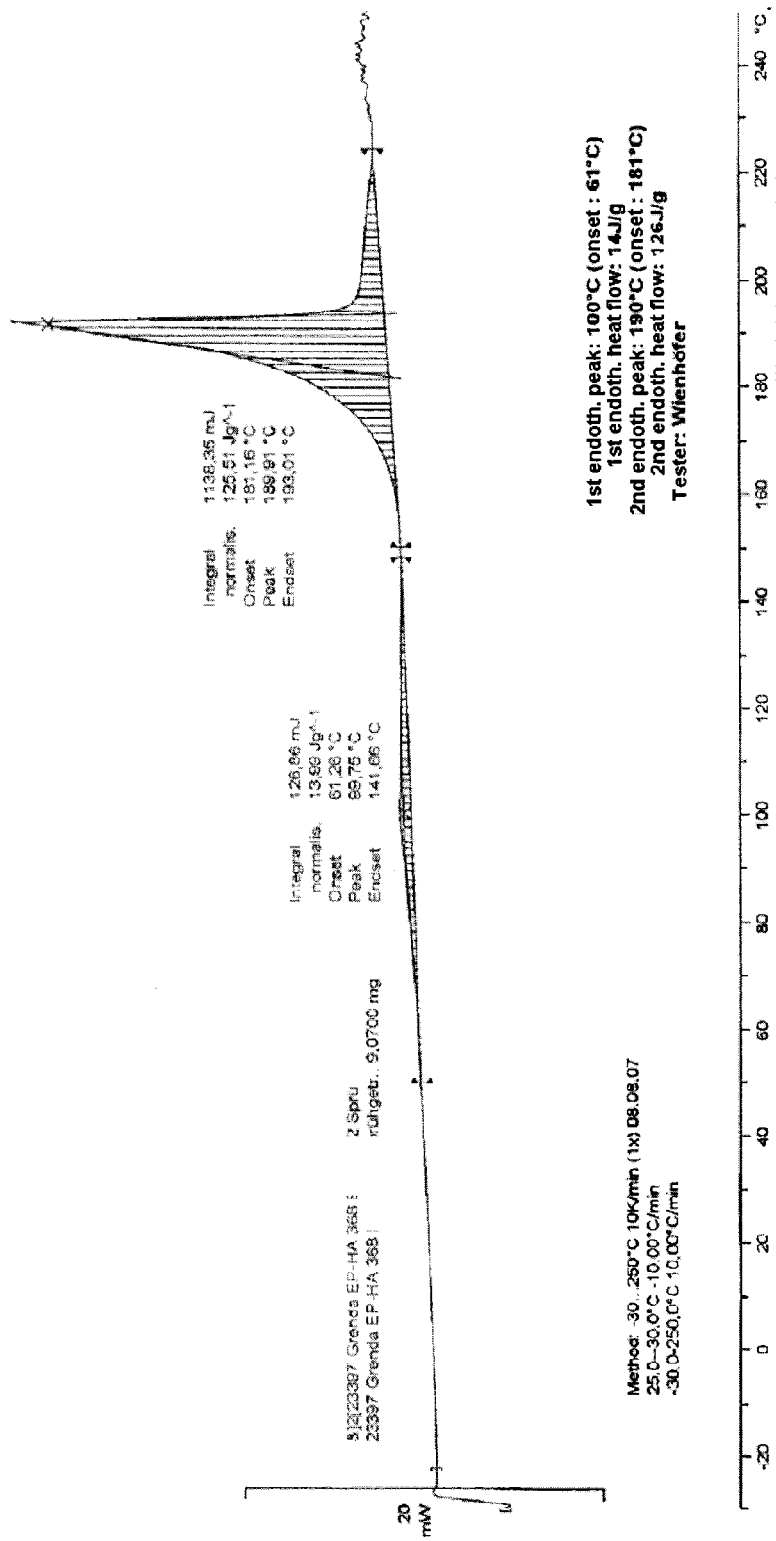
FIG. 8 is a DSC diagram of the β-hydroxyalkylamide described in example 4c.

A noninventive N,N,N',N'-tetrakis(2-hydroxyethyl)cyclohexyl-1,4-diamide having the DSC as per FIG. 8 was prepared.

Figure 10:
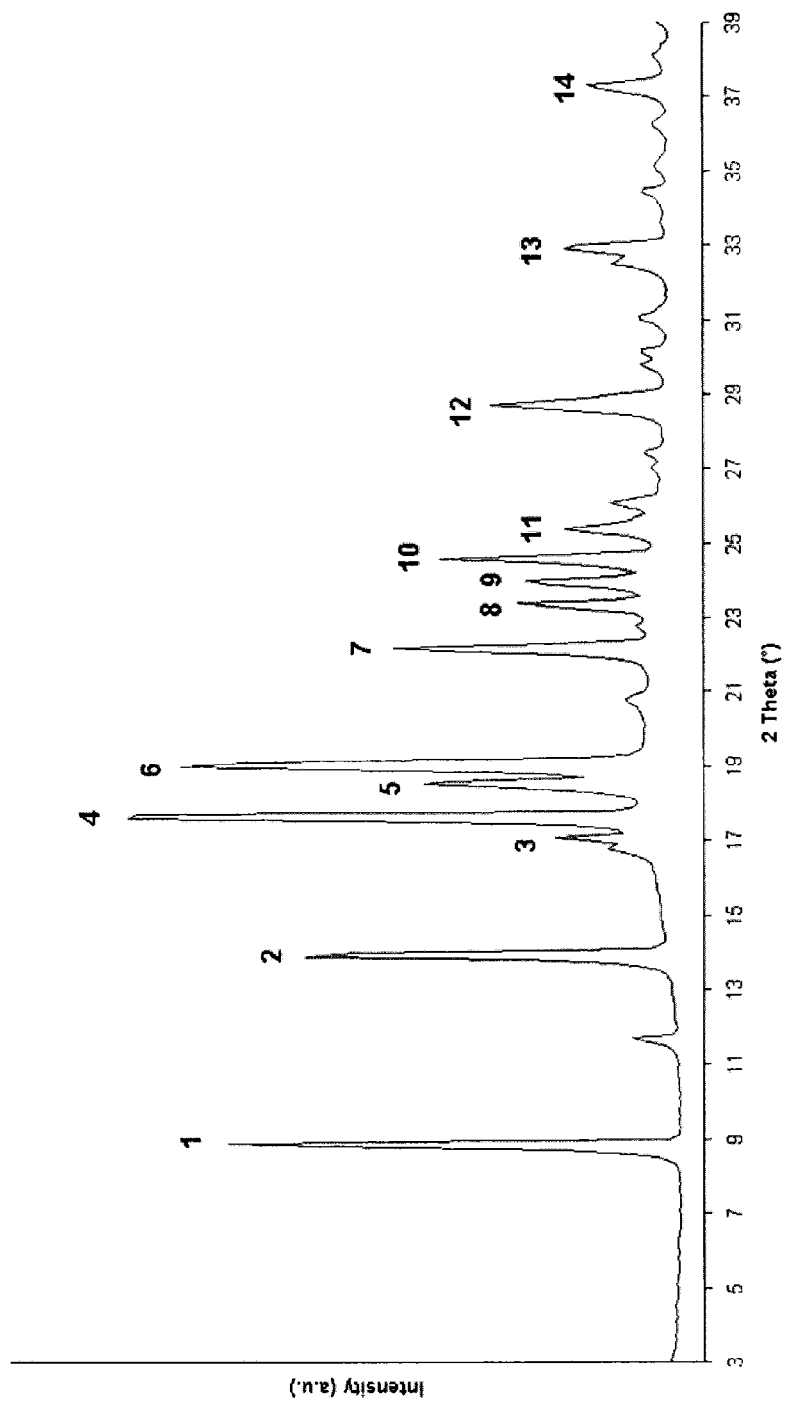
FIG. 10 is a XRPD (x-ray powder diffraction) analysis of the β-hydroxyalkylamide described in example 4c (nonmatting material).

This product exhibits only one endothermic peak in the DSC, at about 190° C., as per FIG. 8, and an XRPD spectrum as per FIG. 10 and table 6. The powder coating material produced from this product does not produce far-reaching matting, but instead exhibits a gloss of 95 scale divisions at the 60 degree angle. Table 4

Example 4d

An N,N,N',N'-tetrakis(2-hydroxyethyl)cyclohexyl-1,4-diamide of the formula XIIA with the product data 4d is prepared in the same way as described in example 1 in an extruder (Werner und Pfleiderer ZSK 30, 32 d). Table 4

This product thus produced is run onto a cooling belt and collected. This material is then subjected to thermal conditioning under reduced pressure in a drying oven at 80° C. for 24 hours, and the product thus obtained is then comminuted.

This product produces far-reaching matting in powder coating materials, with a gloss of 40 scale divisions at the 60° angle. Table 4

TABLE 4

End products from continuous preparation examples 4a-4b and characterization thereof by GC analysis [1]

| Product examples | | 4a | 4b | 4d |
|---|---|---|---|---|
| Starting material | | — | SK 988 | |
| Preparation | | Extruder setting as described in example 1 | Dissolve 4a in deionized water cool slowly crystallize wash with methanol dry under reduced pressure | Extruder setting as described in example 1 thermal condition 24 h 80° C. reduced pressure |
| [1] DEA fraction | % by mass | 2.17 | 0.11 | 1.2 |
| [1] Trans-N,N,N',N'-tetrakis(2-hydroxyethyl)cyclohexyl-1,4-diamide | % by mass | 84.25 | 93.72 | 91.3 |
| [1] Cis-N,N,N',N'-tetrakis(2-hydroxyethyl)cyclohexyl-1,4-diamide | % by mass | 1.60 | 0.11 | 0.66 |
| Σ N,N,N',N'-tetrakis(2-hydroxyethyl)cyclohexyl-1,4-diamide | % by mass | 85.85 | 93.83 | 91.96 |
| Ratio of [1] trans-N,N,N',N'-tetrakis(2-hydroxyethyl)cyclohexyl-1,4-diamide | mol % | 98.1 | 99.9 | 99.3 |
| to [1] cis-N,N,N',N'-tetrakis(2-hydroxyethyl)cyclohexyl-1,4-diamide | mol % | 1.9 | 0.1 | 0.7 |
| OH number | mg KOH/g | 641 | 625 | |
| Base number | — | 24 | 1.1 | |
| DSC: $1^{st}$ endo. peak - Δ H | ° C. - J/g | | 162 - 61 | 158 - 50 |
| DSC: $2^{nd}$ endo. peak - Δ H | ° C. - J/g | | 200 - 128 | 188 - 115 |

| Powder coating data | | | |
|---|---|---|---|
| PC experiment number | | 4b | 4d |
| HAA crosslinker | % by mass | 3.00 | 3.00 |
| CRYLCOAT ® 2617-3 | % by mass | 60.70 | 60.70 |
| KRONOS ® 2160 | % by mass | 35.00 | 35.00 |
| RESIFLOW ® PV 88 | % by mass | 1.00 | 1.00 |
| Benzoin | % by mass | 0.30 | 0.30 |
| Total | % by mass | 100.00 | 100.00 |
| Curing | min@ ° C. | 30 @ 200 | 30 @ 200 |
| Film thickness | μm | 52-55 | 58-68 |
| Gloss at 60° ∢ | Sc. div. | 29-30 | 40 |

TABLE 4-continued

End products from preparation of comparative example 4c and
characterization by GC analysis [1] and powder coating material

| Comparative example | | | 4c |
|---|---|---|---|
| Starting material Preparation | | | allow to cool at RT |
| [1] DEA | % by mass | | 2.87 |
| [1] Trans-N,N,N',N'-tetrakis(2-hydroxyethyl)cyclohexyl-1,4-diamide | % by mass | | 64.11 |
| [1] Cis-N,N,N',N'-tetrakis(2-hydroxyethyl)cyclohexyl-1,4-diamide | % by mass | | 15.84 |
| Σ N,N,N',N'-tetrakis(2-hydroxyethyl)cyclohexyl-1,4-diamide | % by mass | | 79.95 |
| Ratio of [1] trans-N,N,N',N'-tetrakis(2-hydroxyethyl)cyclohexyl-1,4-diamide | mol % | | 80.19 |
| to [1] cis-N,N,N',N'-tetrakis(2-hydroxyethyl)cyclohexyl-1,4-diamide | mol % | | 19.81 |
| OH number | mg KOH/g sample | | — |
| Base number | — | | — |
| DSC: $1^{st}$ endo. peak - Δ H | ° C. - J/g | | |
| DSC: $2^{nd}$ endo. peak - Δ H | ° C. - J/g | | 171 - 87 |
| Powder coating data | | | |
| PC experiment number | | | 4c |
| HAA crosslinker | % by mass | | 3.00 |
| CRYLCOAT ® 2617-3 | % by mass | | 60.70 |
| KRONOS ® 2160 | % by mass | | 35.00 |
| RESIFLOW ® PV 88 | % by mass | | 1.00 |
| Benzoin | % by mass | | 0.30 |
| Total | % by mass | | 100.00 |
| Curing | min@ ° C. | | 30 @ 200 |
| Film thickness | μm | | 65-78 |
| Gloss at 60° ≮ | Sc. div. | | 95 |

[1] Analytical values by GC.
GC after silylation with Silyl 991 (BSTFA-TMCS 99:1) from Macherey und Nagel order No. 701.490.150. Silylation: 1 ml Silyl 991, 1 ml of pyridine, 35 mg of reaction product, 35 mg of C-18 hydrocarbon as internal standard, heat for 30 minutes at 80° C. in a closed ampoule.
OH number: DIN 53240
Base number: DIN 53176

Example 5

A β-hydroxyalkylamide of the formula XIIA was prepared as in example 3a. A single crystal was grown from this product. The inventive of the formula XIIA was investigated by x-ray structural analysis of a single crystal. Comprehensive information on the measurement is compiled in annex 1.
Annex 1
Single-Crystal X-Ray Structural Analysis
Analytical method: Single Crystal X-ray Structure Analysis "2012-0573602-06D"
Report: WHC 11/11 EKS
Sample received: 2011-02-22
Report date: 2011-02-25
Objective: Determination of single-crystal structure.
Compound: N,N,N',N'-tetrakis(2-hydroxyethyl)cyclohexyl-1,4-diamide formula XIIA

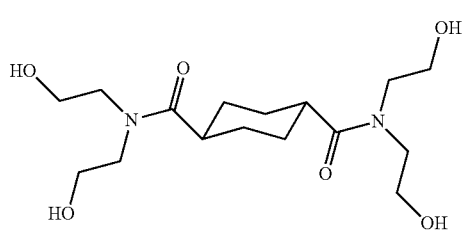 [SMILES: O=C(C1CCC(C(=O)N(CCO)CCO)CC1)N(CCO)CCO]

Figure 12:
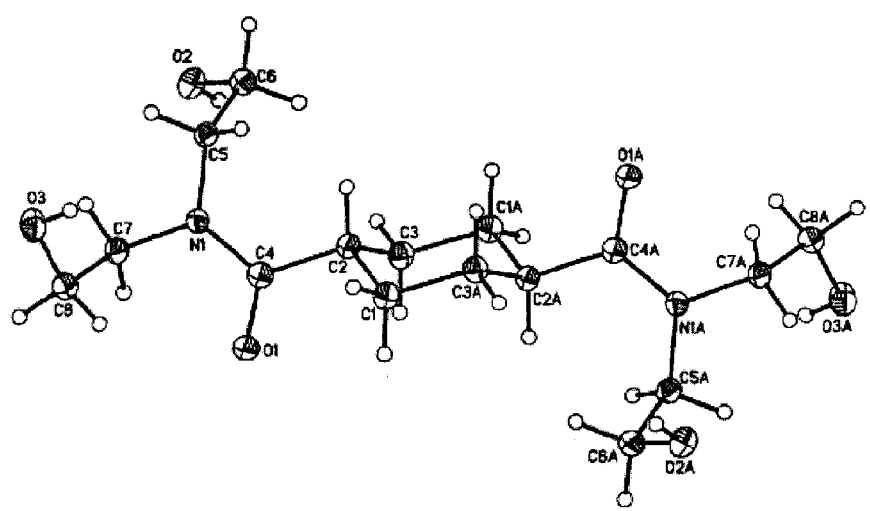
FIG. 12 is an Ortep plot (50%) with numbering scheme.
Figure 13:
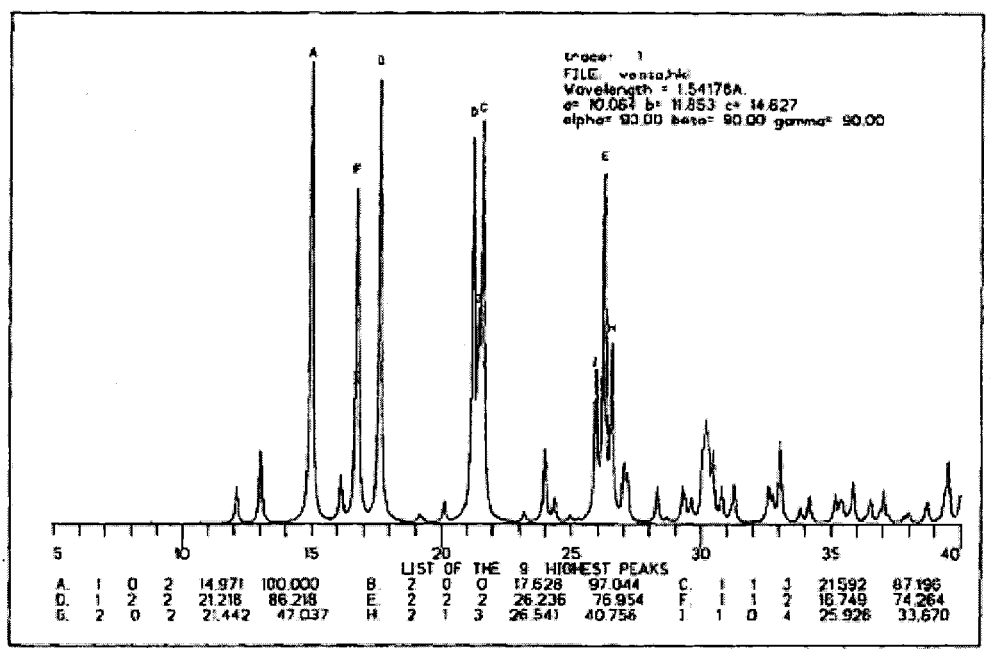
FIG. 13 is a calculated powder diffractogram based on the single-crystal structural determination of N,N,N',N'-tetrakis (2-hydroxyethyl)cyclohexyl-1,4-diamide (vesta sample).

Crystallization: by the chemist.
Crystal dimensions: colorless block, 0.50×0.40×0.40 mm³
Code: vesta
Comments: The asymmetric unit contains half a molecule.
FIG. 12: Ortep Plot (50%) with numbering scheme.

Experimental Details

The single-crystal structure determination was carried out using an instrument from Oxfor Diffraction, which was fitted with a CCD detector (Ruby model), a conventional x-ray tube with $CU_{K\alpha}$ radiation, osmic mirror as monochromator, and a low-temperature unit of the Cryojet type (T=100 K). The data collection was carried out in phi and omega scans. Data collection and reduction took place with Crysalis (Oxford Diffraction 2007).

Structural elucidation and refinement took place with SHELXTL (V. 6.10, Sheldrick, University of Gottingen, 2000). All nonhydrogen atoms were refined anisotropically. The hydrogen atoms were refined as riding groups.

Tables

TABLE a

Crystal data and data relating to structural refinement for vesta.

| | |
|---|---|
| Identification code | vesta |
| Empirical formula | C16 H30 N2 O6 |
| Formula weight | 346.42 |
| Temperature | 100 K |
| Wave length | 1.54178 Å |
| Crystal system | Orthorhombic |
| Space group | Pbca |
| Unit cell | a = 10.06350(10) Å   α = 90°. |
| | b = 11.85290(10) Å   β = 90°. |
| | c = 14.6275(2) Å   γ = 90°. |
| Volume | 1744.79(3) Å$^3$ |
| Z | 4 |
| Density (calculated) | 1.319 mg/m$^3$ |
| Absorption coefficient | 0.832 mm$^{-1}$ |
| F(000) | 752 |
| Crystal dimensions | 0.50 × 0.40 × 0.40 mm$^3$ |
| Theta range for data collection | 6.05 to 65.68°. |
| Index range | −11 ≤ h ≤ 10, −12 ≤ k ≤ 14, −14 ≤ l ≤ 17 |
| Number of reflections collected | 9191 |
| Symmetry-independent reflections | 1482 [R(int) = 0.0345] |
| Completeness to theta = 65.68° | 98.5% |
| Absorption correction | Crysalis |
| Refinement | Full matrix least squares on F$^2$ |
| Data/restraints/parameters | 1482/0/111 |
| Goodness-of-fit on F$^2$ | 1.065 |
| Final R values [I > 2 sigma(I)] | R1 = 0.0316, wR2 = 0.0792 |
| R values (all data) | R1 = 0.0358, wR2 = 0.0817 |
| Largest difference peaks | 0.199 and −0.189 e.Å$^{-3}$ |

TABLE b

Bond lengths [Å] and angles [°] for vesta.

| | |
|---|---|
| O(1)-C(4) | 1.2478(15) |
| O(2)-C(6) | 1.4221(15) |
| O(3)-C(8) | 1.4205(16) |
| N(1)-C(4) | 1.3479(16) |
| N(1)-C(5) | 1.4741(15) |
| N(1)-C(7) | 1.4727(15) |
| C(1)-C(3) #1 | 1.5291(17) |
| C(1)-C(2) | 1.5398(16) |
| C(2)-C(4) | 1.5189(17) |
| C(2)-C(3) | 1.5405(16) |
| C(3)-C(1) #1 | 1.5291(17) |
| C(5)-C(6) | 1.5182(16) |
| C(7)-C(8) | 1.5159(17) |
| C(4)-N(1)-C(5) | 124.59(10) |
| C(4)-N(1)-C(7) | 117.87(10) |
| C(5)-N(1)-C(7) | 117.54(9) |
| C(3) #1-C(1)-C(2) | 110.62(10) |
| C(4)-C(2)-C(1) | 111.04(10) |
| C(4)-C(2)-C(3) | 108.67(10) |
| C(1)-C(2)-C(3) | 110.09(10) |
| C(1) #1-C(3)-C(2) | 111.18(10) |
| O(1)-C(4)-N(1) | 119.97(11) |
| O(1)-C(4)-N(2) | 120.15(10) |
| N(1)-C(4)-C(2) | 119.84(10) |
| N(1)-C(5)-C(6) | 113.66(9) |
| O(2)-C(6)-C(5) | 110.97(10) |
| N(1)-C(7)-C(8) | 113.52(10) |
| O(3)-C(8)-C(7) | 113.31(10) |

Symmetry operations for generating equivalent atoms:
1 −x + 1, −y + 1, −z

TABLE c

Torsional angles [°] for vesta.

| | |
|---|---|
| C(3) #1-C(1)-C(2)-C(4) | 177.11(9) |
| C(3) #1-C(1)-C(2)-C(3) | 56.72(14) |
| C(4)-C(2)-C(3)-C(1) #1 | −178.85(9) |
| C(1)-C(2)-C(3)-C(1) #1 | −57.04(14) |
| C(5)-N(1)-C(4)-O(1) | 176.19(10) |
| C(7)-N(1)-C(4)-O(1) | −3.65(16) |
| C(5)-N(1)-C(4)-C(2) | −6.21(16) |
| C(7)-N(1)-C(4)-C(2) | 173.95(10) |
| C(1)-C(2)-C(4)-O(1) | −54.62(14) |
| C(3)-C(2)-C(4)-O(1) | 66.61(14) |
| C(1)-C(2)-C(4)-N(1) | 127.78(11) |
| C(3)-C(2)-C(4)-N(1) | −110.98(12) |
| C(4)-N(1)-C(5)-C(6) | 80.57(13) |
| C(7)-N(1)-C(5)-C(6) | −99.58(12) |
| N(1)-C(5)-C(6)-O(2) | 61.92(13) |
| C(4)-N(1)-C(7)-C(8) | 86.25(13) |
| C(5)-N(1)-C(7)-C(8) | −93.60(12) |
| N(1)-C(7)-C(8)-O(3) | 73.97(13) |

Symmetry operations for generating equivalent atoms:
1 −x + 1, −y + 1, −z

FIG. 13:

Calculated powder diffractogram based on the single-crystal structure determination of N,N,N',N'-tetrakis(2-hydroxyethyl)cyclohexyl-1,4-diamide (vesta sample)

TABLE 5

Characteristic XRPD peaks (in degrees 2theta) for the β-hydroxyalkylamide of the formula XIIA described in example 3a (matting material)

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

TABLE 6

Characteristic XRPD peaks (in degrees 2theta) for the β-hydroxyalkylamide described in example 4c (nonmatting material)

| Peak # | Degrees 2theta ± 0.2 Grad 2theta | d (Å) |
|---|---|---|
| 1 | 8.90 | 9.93 |
| 2 | 13.90 | 6.37 |
| 3 | 17.10 | 5.18 |
| 4 | 17.60 | 5.04 |
| 5 | 18.50 | 4.79 |
| 6 | 19.00 | 4.67 |
| 7 | 22.20 | 4.00 |
| 8 | 23.40 | 3.80 |
| 9 | 24.00 | 3.71 |
| 10 | 24.60 | 3.62 |
| 11 | 25.40 | 3.50 |
| 12 | 28.70 | 3.11 |
| 13 | 32.00 | 2.80 |
| 14 | 37.30 | 2.41 |

The invention claimed is:

1. A β-hydroxyalkylamide, comprising two or three or four β-hydroxyalkylamide groups per molecule of the formula I:

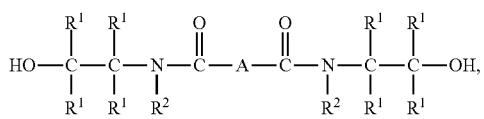

wherein:
R¹ and R² independently of one another are identical or different radicals selected from the group consisting of an alkyl radical, a cycloalkyl radical, an aryl radical, an aralkyl radical and an alkenyl radical having 1-24 carbon atoms, such that the radicals optionally comprise a heteroatom, functional group, or both, R¹ is optionally a hydrogen, and R² is optionally represented by the formula:

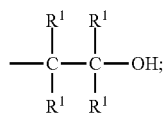

A is represented by A¹:

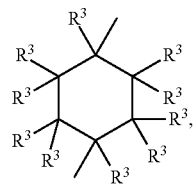

wherein radicals R³ independently of one another are identical or different radicals selected from the group consisting of hydrogen, an alkyl radical, a cycloalkyl radical, an aryl radical, an aralkyl radical, and an alkenyl radical having 1-24 carbon atoms, such that the radicals optionally comprise a heteroatom, a functional group, or both, and two or more substituents R³ are optionally linked with one another to form rings;
the β-hydroxyalkylamide is present in solid form below 150° C.;
wherein the β-hydroxyalkylamide has a trans content of greater than or equal to 70 mol % based on the total amount of all of the isomers of the β-hydroxyalkylamide;
wherein the β-hydroxyalkylamide has two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.; and
wherein a ratio of the enthalpies of endothermic peak 1 to endothermic peak 2 is 1:1 to 1:5.

2. The β-hydroxyalkylamide of claim 1, wherein the β-hydroxyalkylamide derives from at least one β-hydroxyalkylamine comprising an alkyl group having at least 2 to 10 carbon atoms in the hydrocarbon framework, such that the alkyl groups are optionally linear, branched or cyclic, the alkyl groups are optionally substituted with at least one heteroatom, and the alkyl groups optionally comprise a functional group an additional alkyl radical on a nitrogen.

3. The β-hydroxyalkylamide of claim 1, comprising at least one β-hydroxyalkylamide formed from an N-alkyl-1,2-alkanolamine, an N,N,-bis-2-hydroxyalkylamine, or both, and an ester of a cyclohexanedicarboxylic acid.

4. The β-hydroxyalkylamide of claim 1 comprising a β-hydroxyalkyamide derived from at least one β-hydroxyalkylamine of formula II and/or III, formulae II:

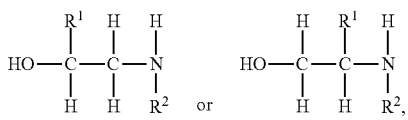

wherein
R¹ is hydrogen, methyl, ethyl, or propyl; and
R² is methyl;
formulae III:

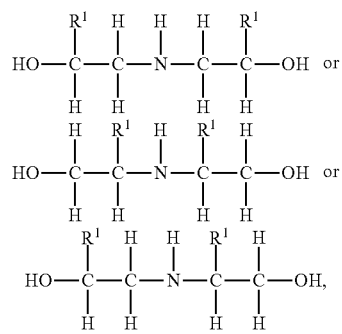

wherein radicals R¹ simultaneously or independently of one another are hydrogen, methyl, ethyl, or propyl.

5. The β-hydroxyalkylamide of claim 1, comprising a β-hydroxyalkylamide derived from the following compounds: diethanolamine (DEA), di-isopropropanolamine (DIPA), di-sec-butanolamine, N-methylethanolamine, N-methylisopropanolamine.

6. The β-hydroxyalkylamide of claim 1, comprising a β-hydroxyalkylamide derived from at least one compound comprising the substituent A, said compound being a 1,4-substituted cyclohexanedicarboxylic acid derivative.

7. The β-hydroxyalkylamide of claim 1, comprising a β-hydroxyalkylamide derived from at least one compound of formula IV:

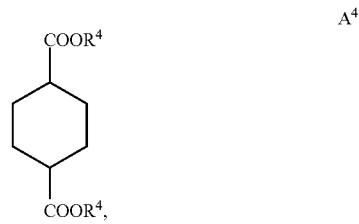

wherein radicals R⁴ simultaneously or independently of one another are methyl, ethyl, propyl, or butyl.

8. The β-hydroxyalkylamide of claim 1, comprising a β-hydroxyalkylamide derived from at least one 1,4-substituted cyclohexanedicarboxylic ester.

9. The β-hydroxyalkylamide of claim 1, comprising at least one β-hydroxylalkylamide of the following formulae:

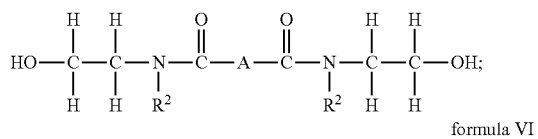
formula V

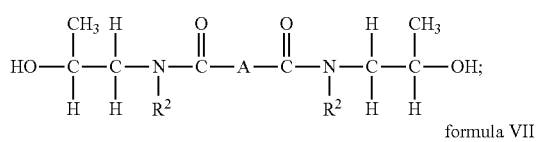
formula VI

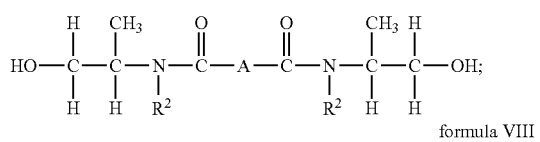
formula VII

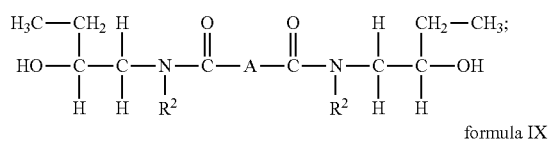
formula VIII

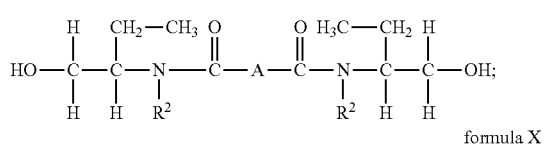
formula IX

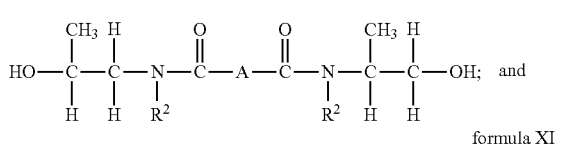
formula X

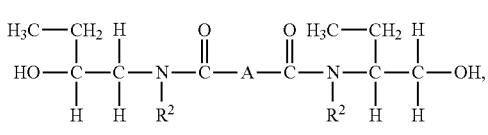
formula XI wherein:
$R^2$ is methyl, or:

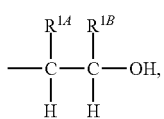

such that $R^{1A}$ is hydrogen and $R^{1B}$ is methyl, ethyl, or propyl, or $R^{1A}$ is methyl, ethyl, or propyl and $R^{1B}$ is hydrogen;
A is a 1,4-disubstituted cyclohexane ring of the formula:

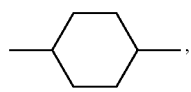

wherein a trans content of A is ≥70 mol %; and
the β-hydroxyalkylamide is in solid form below 150° C.;
wherein the β-hydroxyalkylamide has two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.; and
wherein a ratio of the enthalpies of endothermic peak 1 to endothermic peak 2 is 1:1 to 1:5.

10. The β-hydroxyalkylamide of claim 1, formed from at least one dialkyl 1,4-cyclohexyldicarboxylate having a trans content, based on the position of the carboxyl groups on the cyclohexyl ring, of greater than or equal to 70 mol %.

11. The β-hydroxyalkylamide of claim 1, formed from a dimethyl 1,4-cyclohexyldicarboxylate and diethanolamine, having four β-hydroxyalkylamide groups per molecule, of the formula XII:

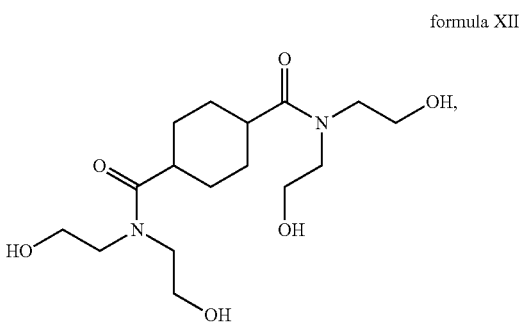 [SMILES: O=C(C1CCC(C(=O)N(CCO)CCO)CC1)N(CCO)CCO]
formula XII wherein a trans content on the cyclohexyl ring is greater than or equal to 70 mol %.

12. The β-hydroxyalkylamides of claim 1, comprising a β-hydroxyalkylamide present in solid form below 150° C.

13. A method for the solvent-free, continuous preparation of the β-hydroxyalkylamide of claim 1, the method comprising reacting reactants continuously in an extruder, intensive compounder, intensive mixer, or a static mixer with intensive mixing to form a β-hydroxyalkylamide, wherein
A is a 1,4-disubstituted cyclohexane ring of the formula:

such that a trans content of A is ≥70 mol %.

14. The method of claim 13, wherein the reactants comprise a dialkyl 1,4-cyclohexyldicarboxylate having a trans content on the cyclohexyl ring of greater than or equal to 70 mol % and present in solid form below 150° C.

15. The method of claim 13, wherein the reactants comprise a dialkyl 1,4-cyclohexayldicarboxlylate.

16. The method of claim 13, comprising reacting the reactants with intense mixing and a brief reaction with a supply of heat at temperatures >50° C. followed by isolation of the β-hydroxyalkylamide by cooling.

17. The method of claim 13, wherein a residence time of the reactants is 3 seconds to 15 minutes.

18. The method of claim 13, wherein the reaction occurs in a single-, twin- or multiscrew extruder, annular extruder or planetary roller extruder.

19. The method of claim 13, wherein a temperature in the extruder, intensive compounder, intensive mixer or static mixer is 50 to 325° C.

20. The method of claim 13, wherein the reactants comprise dimethyl 1,4-cyclohexyldicarboxylate and diethanolamine, and the β-hydroxyalkylamide comprises four β-hydroxyalkylamide groups per molecule, and is represented by formula XII:

formula XII

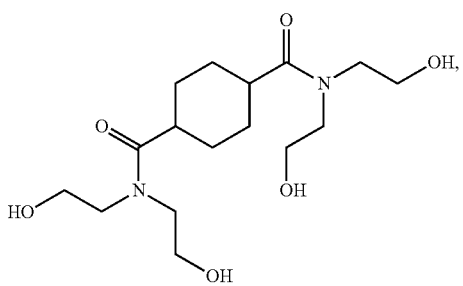

such that a trans content on the cyclohexyl ring of greater than or equal to 70 mol %.

21. A method for producing a coating having a matt surface, the method comprising apply the β-hydroxyalkylamide of claim 1 to a substrate.

22. A crosslinker for a polymer comprising carboxyl groups, the crosslinker comprising the β-hydroxyalkylamide of claim 1.

23. A powder coating material, comprising the crosslinker of claim 22.

24. The method of claim 21, wherein the matt coating has <50 gloss units, measured as reflectometer values according to DIN 67530/ISO 2813 at an incident angle of 60°.

25. The β-hydroxyalkylamide of claim 11, comprising an N,N,N',N'-tetrakis(2-hydroxyethyl)cyclohexyl-1,4-diamide of formula XIIA:

XIIA

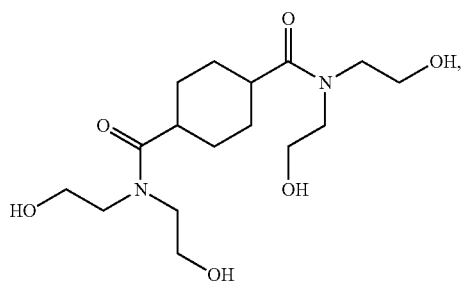

having the following parameters:
  a trans content on the cyclohexyl ring of greater than or equal to 70 mol %, based on the total amount of all of the isomers of N,N,N',N'-tetrakis(2-hydroxyethyl)cyclohexyl-1,4-diamide;
  two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.;
  a ratio of the enthalpies of endothermic peak 1 to endothermic peak 2 is 1:1 to 1:5; and
  a XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43. |

26. The β-hydroxyalkylamide of claim 25, wherein the N,N,N',N'-tetrakis(2-hydroxyethyl)cyclohexyl-1,4-diamide has a trans content on the cyclohexyl ring of greater than or equal to 92 mol %, based on a total amount of all of the isomers of N,N,N',N'-tetrakis(2-hydroxyethyl)-cyclohexyl-1,4-diamide.

27. The β-hydroxyalkylamide of claim 25, wherein the β-hydroxyalkylamide of the formula XIIA is present in solid form below 175° C.

28. The β-hydroxyalkylamide of claim 25, wherein a concentration of all of the isomers of N,N,N',N'-tetrakis(2-hydroxyethyl)cyclohexyl-1,4-diamide in the end product after its preparation is 75% by mass.

29. The β-hydroxyalkylamide of claim 25, wherein a ratio of the enthalpies of endothermic peak 1 (~160° C.) to endothermic peak 2 (~190° C.) is 1:1 to 1:3.

30. The β-hydroxyalkylamide of claim 25, wherein the N,N,N',N'-tetrakis(2-hydroxyethyl)cyclohexyl-1,4-diamide of formula XIIA:

XIIA

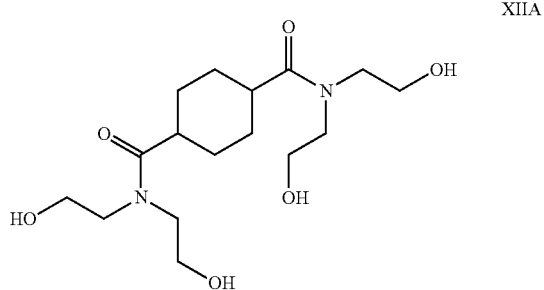 [SMILES: O=C(C1CCC(C(=O)N(CCO)CCO)CC1)N(CCO)CCO]

has the following parameters:
  a trans content on the cyclohexyl ring of greater than or equal to 70 mol %, based on the total amount of all of the isomers of N,N,N',N'-tetrakis(2-hydroxyethyl)cyclohexyl-1,4-diamide;
  two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.;
  a ratio of the enthalpies of endothermic peak 1 to endothermic peak 2 is 1:1 to 1:5;
  a XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |

-continued

| Peak # | Degrees 2theta ± 0.2 degree 2theta | d (Å) |
|---|---|---|
| 5 | 21.60 | 4.11 |
| 6 | 26.00 | 3.43; and | according to x-ray structural analysis of a single crystal, has the following crystal parameters:

| | | |
|---|---|---|
| Crystal system: | Orthorhombic; | |
| Space group: | Pbca; | |
| Unit cell dimensions: | a = 10.06350(10) Å | α = 90°, |
| | b = 11.85290(10) Å | β = 90°, |
| | c = 14.6275(2) Å | γ = 90°, |
| Volume: | 1744.79(3) Å³. | |

31. A method for the discontinuous preparation of an N,N,N',N'-tetrakis(2-hydroxyethyl)cyclohexyl-1,4-diamide according to formula XIIA:

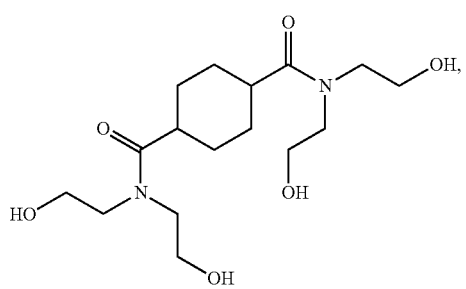

XIIA the method comprising reacting dimethyl 1,4-cyclohexyl-dicarboxylate and diethanolamine in a solvent in an extruder, intensive compounder, intensive mixer or static mixer, wherein the N,N,N',N'-tetrakis(2-hydroxyethyl)cyclohexyl-1,4-diamide has the following parameters:
  a trans content on the cyclohexyl ring of greater than or equal to 70 mol %, based on the total amount of all of the isomers of N,N,N',N'-tetrakis(2-hydroxyethyl)cyclohexyl-1,4-diamide;
  two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.;
  a ratio of the enthalpies of endothermic peak 1 to endothermic peak 2 is 1:1 to 1:5; and
  an XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

32. The method of claim 31, wherein the reacting occurs at temperatures from 20 to 120° C.

33. The method of claim 31, wherein an amount of solvent added is greater than 10% by weight, based on an total amount of all of the reactants.

34. A method for the discontinuous preparation of an N,N,N',N'-tetrakis(2-hydroxyethyl)cyclohexyl-1,4-diamide according to formula XIIA:

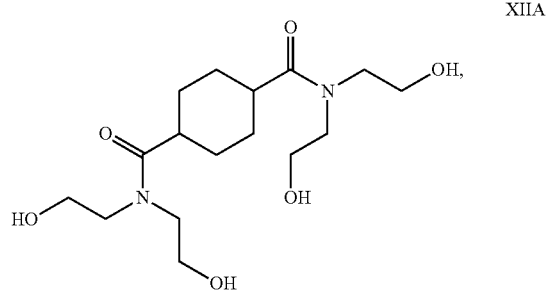

XIIA the method comprising reacting dimethyl 1,4-cyclohexyl-dicarboxylate and diethanolamine in closed apparatus under pressure at temperatures from 60 to 140° C. without addition of solvents, wherein the N,N,N',N'-tetrakis(2-hydroxyethyl)cyclohexyl-1,4-diamide has the following parameters:
  a trans content on the cyclohexyl ring of greater than or equal to 70 mol %, based on the total amount of all of the isomers of N,N,N',N'-tetrakis(2-hydroxyethyl)cyclohexyl-1,4-diamide that are present;
  two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.;
  a ratio of the enthalpies of endothermic peak 1 to endothermic peak 2 is 1:1 to 1:5; and
  an XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43 |

35. The method of claim 34, further comprising recrystallizing the N,N,N',N'-tetrakis(2-hydroxyethyl)cyclohexyl-1,4-diamide, wherein the reacting occurs at temperatures from 20 to 140° C.

36. The method of claim 34, wherein:
  the method further comprises:
    recrystallizing the N,N,N',N'-tetrakis(2-hydroxyethyl)cyclohexyl-1,4-diamide; or
    thermally conditioning the N,N,N',N'-tetrakis(2-hydroxyethyl)cyclohexyl-1,4-diamide at temperatures of 50-100° C. for.

37. The method of claim 34 wherein an x-ray structural analysis of a single crystal of the N,N,N',N'-tetrakis-(2-hydroxyethyl)cyclohexyl-1,4-diamide, has the following parameters:

| Crystal system: | Orthorhombic | |
|---|---|---|
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å³. | |

38. A process for producing a coating, the process comprising applying the β-hydroxyalkylamide of claim 25 to a substrate.

39. The process of claim 38, wherein an x-ray structural analysis of a single crystal of the N,N,N',N'-tetrakis(2-hydroxyethyl)cyclohexyl-1,4-diamide, has the following parameters:

| Crystal system: | Orthorhombic | |
|---|---|---|
| Space group: | Pbca | |
| Unit cell dimensions: | a = 10.06350(10) Å | α = 90°. |
| | b = 11.85290(10) Å | β = 90°. |
| | c = 14.6275(2) Å | γ = 90°. |
| Volume: | 1744.79(3) Å³. | |

40. A powder coating material, comprising the β-hydroxyalkylamide of claim 25.

41. The method of claim 38 which produces a coating having a matt surface with <50 gloss units, measured as reflectometer values according to DIN 67530/ISO 2813 at an incident angle of 60°.

42. A β-hydroxyalkylamide, comprising two or three or four β-hydroxyalkylamide groups per molecule of the formula I:

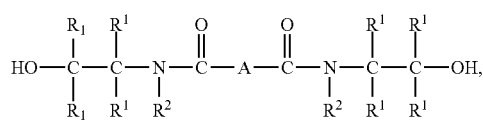

I wherein:
$R^1$ and $R^2$ independently of one another are identical or different radicals selected from the group consisting of an alkyl radical, a cycloalkyl radical, an aryl radical, an aralkyl radical and an alkenyl radical having 1-24 carbon atoms, such that the radicals optionally comprise a heteroatom, functional group, or both, $R^1$ is optionally a hydrogen, and $R^2$ is optionally represented by the formula:

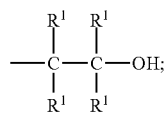

A is represented by $A^1$:

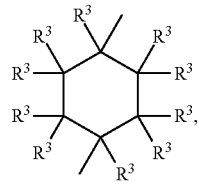

$A^1$ wherein radicals $R^3$ independently of one another are identical or different radicals selected from the group consisting of hydrogen, an alkyl radical, a cycloalkyl radical, an aryl radical, an aralkyl radical, and an alkenyl radical having 1-24 carbon atoms, such that the radicals optionally comprise a heteroatom, a functional group, or both, and two or more substituents $R^3$ are optionally linked with one another to form rings;

wherein the β-hydroxyalkylamide is present in solid form below 150° C.;

wherein the β-hydroxyalkylamide has a trans content of greater than or equal to 70 mol % based on the total amount of all of the isomers of the β-hydroxyalkylamide;

two endothermic peaks according to DSC analysis (differential scanning calorimetry), where peak 1 is situated in the region of 140-170° C., with a maximum of 155-165° C., and peak 2 is situated in the region of 170-210° C., with a maximum of 175-207° C.;

a ratio of the enthalpies of endothermic peak 1 to endothermic peak 2 is 1:1 to 1:5; and a XRPD spectrum of the powder sample in an x-ray diffractometer, measured with Cu Kα radiation (1.541 Å) has the following peaks:

| Peak # | Degrees 2theta ± 0.2 degree 2theta | d (Å) |
|---|---|---|
| 1 | 14.90 | 5.94 |
| 2 | 16.70 | 5.31 |
| 3 | 17.40 | 5.09 |
| 4 | 21.20 | 4.19 |
| 5 | 21.60 | 4.11 |
| 6 | 26.00 | 3.43. |

* * * * *